(12) United States Patent
Ying et al.

(10) Patent No.: US 10,975,350 B2
(45) Date of Patent: Apr. 13, 2021

(54) CELL CULTURE SUBSTRATE AND METHOD OF MAKING THEREOF

(71) Applicant: AGENCY FOR SCIENCE, TECHNOLOGY AND RESEARCH, Singapore (SG)

(72) Inventors: Jackie Y. Ying, Singapore (SG); Nandanan Erathodiyil, Singapore (SG); Karthikeyan Narayanan, Singapore (SG); Andrew C. A. Wan, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 392 days.

(21) Appl. No.: 15/780,236

(22) PCT Filed: Nov. 30, 2016

(86) PCT No.: PCT/SG2016/050587
§ 371 (c)(1),
(2) Date: May 30, 2018

(87) PCT Pub. No.: WO2017/095333
PCT Pub. Date: Jun. 8, 2017

(65) Prior Publication Data
US 2018/0355310 A1    Dec. 13, 2018

(30) Foreign Application Priority Data
Nov. 30, 2015   (SG) .............................. 10201509845Q

(51) Int. Cl.
| | | |
|---|---|---|
| *C12N 5/00* | (2006.01) | |
| *C12N 5/0775* | (2010.01) | |
| *B82Y 30/00* | (2011.01) | |
| *B82Y 5/00* | (2011.01) | |

(52) U.S. Cl.
CPC ......... *C12N 5/0068* (2013.01); *C12N 5/0662* (2013.01); *B82Y 5/00* (2013.01); *B82Y 30/00* (2013.01); *C12N 2533/30* (2013.01); *C12N 2537/00* (2013.01); *C12N 2539/00* (2013.01)

(58) Field of Classification Search
CPC .............. C12N 5/0068; C12N 2533/30; C12N 2537/00; C12N 2539/00; C12N 5/0662; B82Y 30/00; B82Y 5/00
See application file for complete search history.

(56) References Cited

U.S. PATENT DOCUMENTS

| | | |
|---|---|---|
| 5,449,383 A | 9/1995 | Chatelier et al. |
| 6,214,618 B1 | 4/2001 | Hillegas et al. |
| 2005/0214803 A1 | 9/2005 | Wang |
| 2012/0052579 A1 | 3/2012 | Shannon et al. |
| 2014/0025586 A1 | 1/2014 | Lowe |
| 2014/0315300 A1 | 10/2014 | Oh et al. |

FOREIGN PATENT DOCUMENTS

| | | |
|---|---|---|
| KR | 10-20130043921 B1 | 5/2013 |
| KR | 10-20140125662 A | 10/2014 |
| WO | 2008112560 A1 | 9/2008 |
| WO | WO 2010019875 A2 | 2/2010 |
| WO | WO 2013036585 A1 | 3/2013 |
| WO | 2014/168585 A1 | 10/2014 |

OTHER PUBLICATIONS

Hopper et al., Amine functionalized nanodiamond promotes cellular adhesion, proliferation and neurite outgrowth. Biomedical Materials, vol. 9 (2014) 045009. (Year: 2014).*
Wang et al., Multifunctional biodegradable polyacrylamide nanocarriers for cancer theranostics—a "see and treat" strategy. ACS Nano, vol. 6, No. 8 (2012) pp. 6843-6851 (Year: 2012).*
IP Office of Singapore—Notification of Transmittal of the International Search Report & the Written Opinion of the International Searching Authority, or the Declaration, with the International Search Report & Written Opinion dated Feb. 26, 2017 for International Application No. PCT/SG2016/050587 (11 pgs).
Response to Written Opinion—Chapter II Demand with Article 34 Amendment filed Jun. 22, 2017 with the IP Office of Singapore for International Application No. PCT/SG2016/050587 (25 pgs).
IP Office of Singapore—Written Opinion of the International Preliminary Examining Authority (IPEA) dated Aug. 22, 2017 for International Application No. PCT/SG2016/050587 (6 pgs).
IP Office of Singapore—Notification of Transmittal of International Preliminary Report on Patentability dated Dec. 28, 2017 for International Application No. PCT/SG2016/050587 (19 pgs).
Hopper, A.P., et al., "Amine functionalized nanodiamond promotes cellular adhesion, proliferation and neurite outgrowth." *Biomed. Mater.*, Jul. 16, 2014, vol. 9, No. 4, pp. 045009:1-11.
Knibbs, R.N., et al., "Sustained high-yield production of recombinant proteins in transiently transfected COS-7 cells grown on trimethylamine-coated (Hillex) Microcarrier beads." *Biotechnol. Prog.*, Feb. 28, 2003, vol. 19, No. 1, pp. 9-13.

(Continued)

*Primary Examiner* — Kara D Johnson
(74) *Attorney, Agent, or Firm* — Womble Bond Dickinson (US) LLP

(57) ABSTRACT

A cell culture substrate comprising a substrate having a coating of a plurality of amine functionalized nanoparticles is disclosed. In one embodiment, the amine functionalized nanoparticle is a polymer of an acrylamide monomer, a cross-linker and an amine monomer. There is also provided a method of making the cell culture substrate either by drying the amine functionalized nanoparticles when spread onto the said substrate or by covalent linkages of the substrate with thiol terminated nanoparticles. In addition, there is provided a method of culturing stem cells on the cell culture substrate having a coating of a plurality of the amine functionalized nanoparticles thereon.

20 Claims, 14 Drawing Sheets

(56) References Cited

OTHER PUBLICATIONS

Sperling, R.A., et al., "Surface modification, functionalization and bioconjugation of colloidal inorganic nanoparticles." *Phil. Tran. R. Soc. A.*, Feb. 15, 2010, vol. 368, No. 1915, pp. 1333-1383.

Beers et al., "Passaging and colony expansion of human pluripotent stem cells by enzyme-free dissociation in chemically defined culture conditions" Nature Protocols, vol. 7, No. 11, Oct. 25, 2012, pp. 2029-2040.

Bergstrom et al., "Xeno-free culture of human pluripotent stem cells" Methods in Molecular Biology, vol. 767, Jul. 2011, pp. 125-136.

Brafman et al., "Long-term human pluripotent stem cell self-renewal on synthetic polymer surfaces" Biomaterials, vol. 31, No. 34, Sep. 15, 2010, pp. 9135-9144.

Celiz et al., "Materials for stem cell factories of the future" Nature Materials, vol. 13, No. 6, May 21, 2014, pp. 570-579.

Chen et al., "Nanotopography influences adhesion, spreading, and self-renewal of human embryonic stem cells" ACS Nano, vol. 6, No. 5, Apr. 16, 2012, pp. 4094-4103.

Daley et al., "Prospects for stem cell-based therapy" Cell, vol. 132, No. 4, Feb. 22, 2008, pp. 544-548.

Dhandayuthapani et al., "Polymeric scaffolds in tissue engineering application: A review" International Journal of Polymer Science, vol. 2011, Sep. 11, 2011, pp. 1-19.

Irwin et al., "Engineered polymer-media interfaces for the long-term self-renewal of human embryonic stem cells" Biomaterials, vol. 32, No. 29, Jul. 20, 2011, pp. 6912-6919.

Klim et al., "A defined glycosaminoglycan-binding substratum for human pluripotent stem cells" Nature Methods, vol. 7, No. 12, Nov. 14, 2010, pp. 989-994.

Kurosawa "Methods for inducing embryoid body formation: In vitro differentiation system of embryonic stem cells" Journal of Bioscience and Bioengineering, vol. 103, No. 5, May 2007, pp. 389-398.

Legate et al., "Genetic and cell biological analysis of integrin outside-in signaling" Genes & Development, vol. 23, No. 4, Feb. 15, 2009, pp. 397-418.

Ludwig et al., "Derivation of human embryonic stem cells in defined conditions" Nature Biotechnology, vol. 24, No. 2, Jan. 1, 2006, pp. 185-187.

Maitra et al., "Genomic alterations in cultured human embryonic stem cells" Nature Genetics, vol. 37, No. 10, Sep. 4, 2005, pp. 1099-1103.

Mei et al., "Combinatorial development of biomaterials for clonal growth of human pluripotent stem cells" Nature Materials, vol. 9, No. 9, Aug. 22, 2010, pp. 768-778.

Melkoumian et al., "Synthetic peptide-acrylate surfaces for long-term self-renewal and cardiomyocyte differentiation of human embryonic stem cells" Nature Biotechnology, vol. 28, No. 6, May 30, 2010, pp. 606-609.

Moffat et al., "A novel polyacrylamide magnetic nanoparticle contrast agent for molecular imaging using MRI" Molecular Imaging, vol. 2, No. 4, Oct. 1, 2003 pp. 324-332.

Murphy et al., "Materials as stem cell regulators" Nature Materials, vol. 13, No. 6, May 21, 2014, pp. 547-557.

O'Brien "Biomaterials & scaffolds for tissue engineering" Materials Today, vol. 14, No. 3, Mar. 2011, pp. 88-95.

Pan et al., "Stem cell pluripotency and transcription factor" Cell Research, vol. 12, Dec. 2002, pp. 321-329.

Saha et al., "Surface-engineered substrates for improved human pluripotent stem cell culture under fully defined conditions" Proceedings of the National Academy of Sciences of the United States of America, vol. 108, No. 46, Nov. 15, 2011, pp. 18714-18719.

Saha et al., "Technical challenges in using human induced pluripotent stem cells to model disease" Cell Stem Cell, vol. 5, No. 6, Dec. 4, 2009, pp. 584-595.

Spits et al., "Recurrent chromosomal abnormalities in human embryonic stem cells" Nature Biotechnology, vol. 26, No. 12, Nov. 23, 2008, pp. 1361-1363.

Takahashi et al., "Induction of pluripotent stem cells from adult human fibroblasts by defined factors" Cell, vol. 131, Issue 5, Nov. 30, 2007, pp. 861-872.

Thomson et al., "Embryonic stem cell lines derived from human blastocysts" Science, vol. 282, Issue 5391, Nov. 6, 1998, pp. 1145-1147.

Trappmann et al., "Extracellular-matrix tethering regulates stem-cell fate" Nature Materials, vol. 11, No. 7, May 27, 2012, pp. 642-649.

Villa-Diaz et al., "Synthetic polymer coatings for long-term growth of human embryonic stem cells" Nature Biotechnology, vol. 28, No. 6, May 30, 2010, pp. 581-583.

Weissbein et al., "Genome maintenance in pluripotent stem cells" Journal of Cell Biology, vol. 204, No. 2, Jan. 20, 2014, pp. 153-163.

Xu et al., "Feeder-free growth of undifferentiated human embryonic stem cells" Nature Biotechnology, vol. 19, No. 10, Oct. 1, 2001, pp. 971-974.

Yao et al., "Long-term self-renewal and directed differentiation of human embryonic stem cells in chemically defined conditions" Proceedings of the National Academy of Sciences of the United States of America, vol. 103, No. 18, May 2, 2006, pp. 6907-6912.

Yu et al., "Induced pluripotent stem cell lines derived from human somatic cells" Science, vol. 318, Issue 5858, Nov. 20, 2007, pp. 1917-1920.

The First Office Action and Search Report for Chinese counterpart Patent Application No. 201680064381.7, dated Jan. 20, 2021, 19 pages.

* cited by examiner

[Fig. 1]
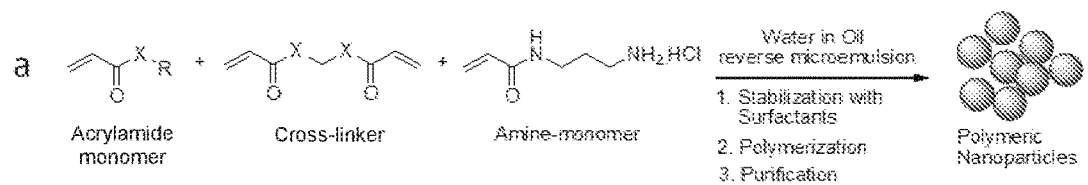
[Fig. 2]
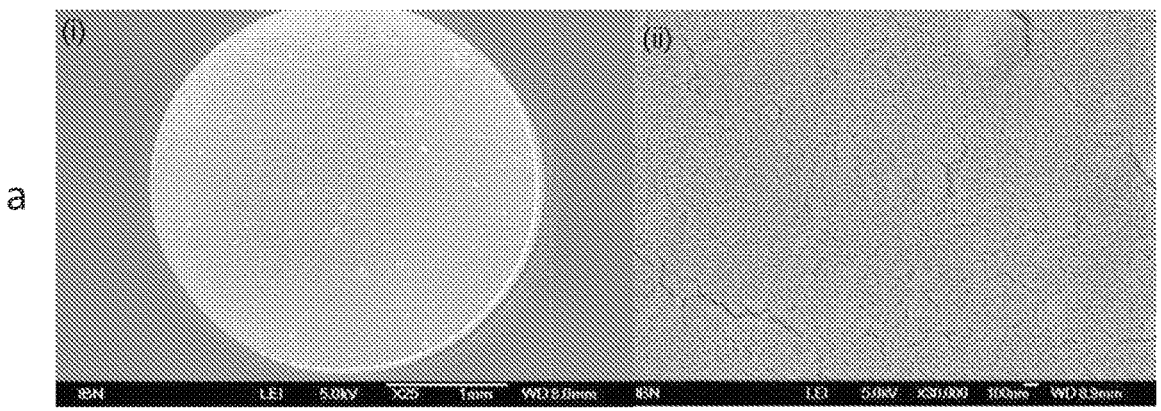

[Fig. 2]
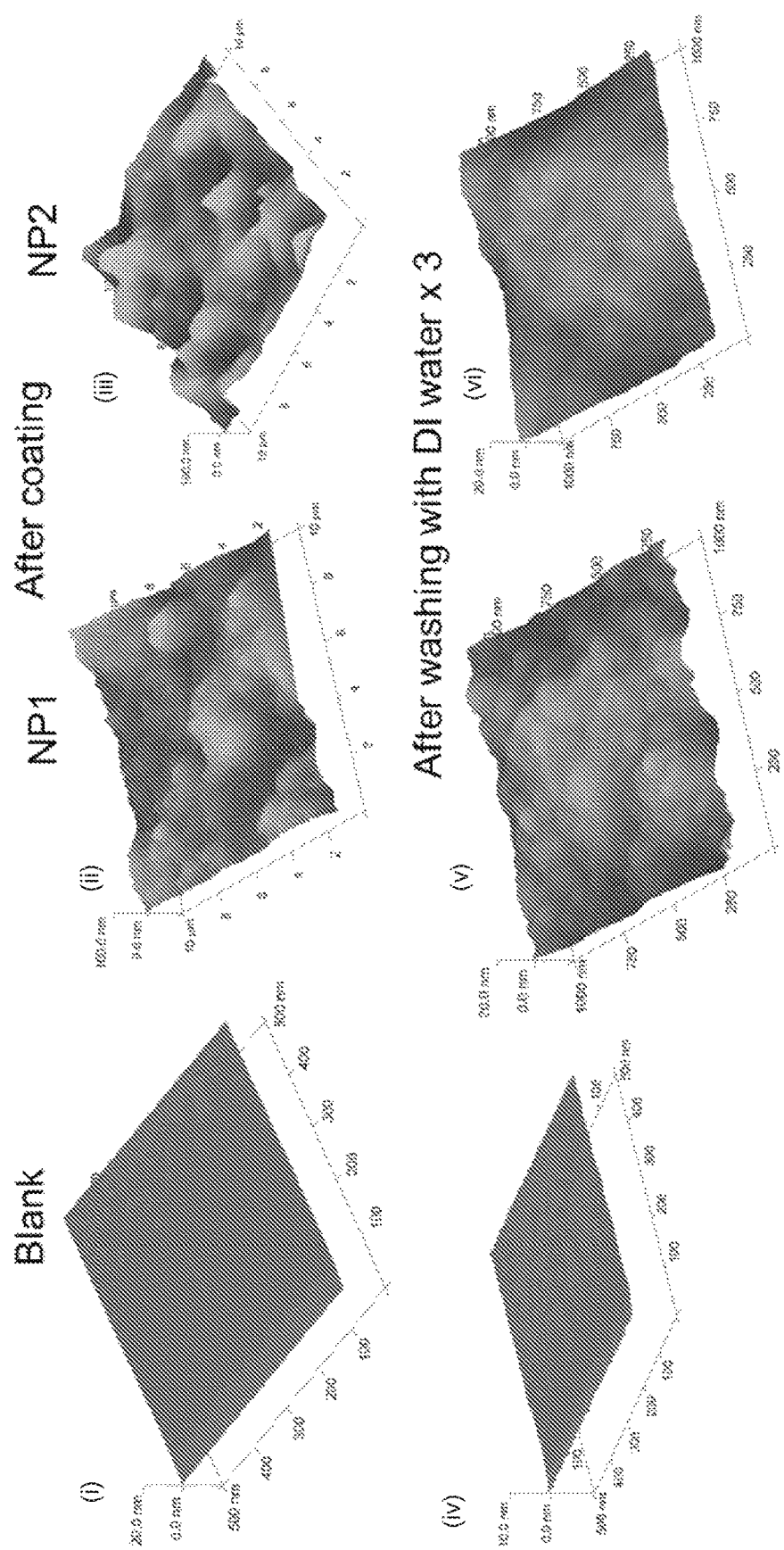

[Fig. 2]
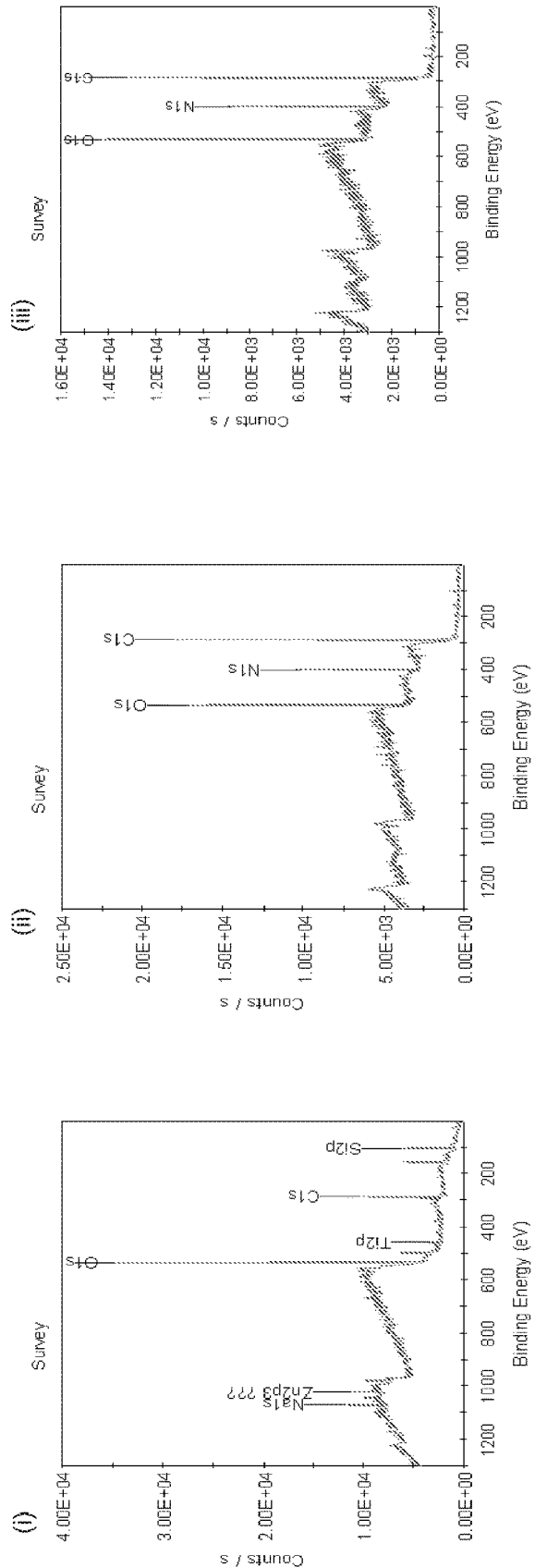

[Fig. 3]
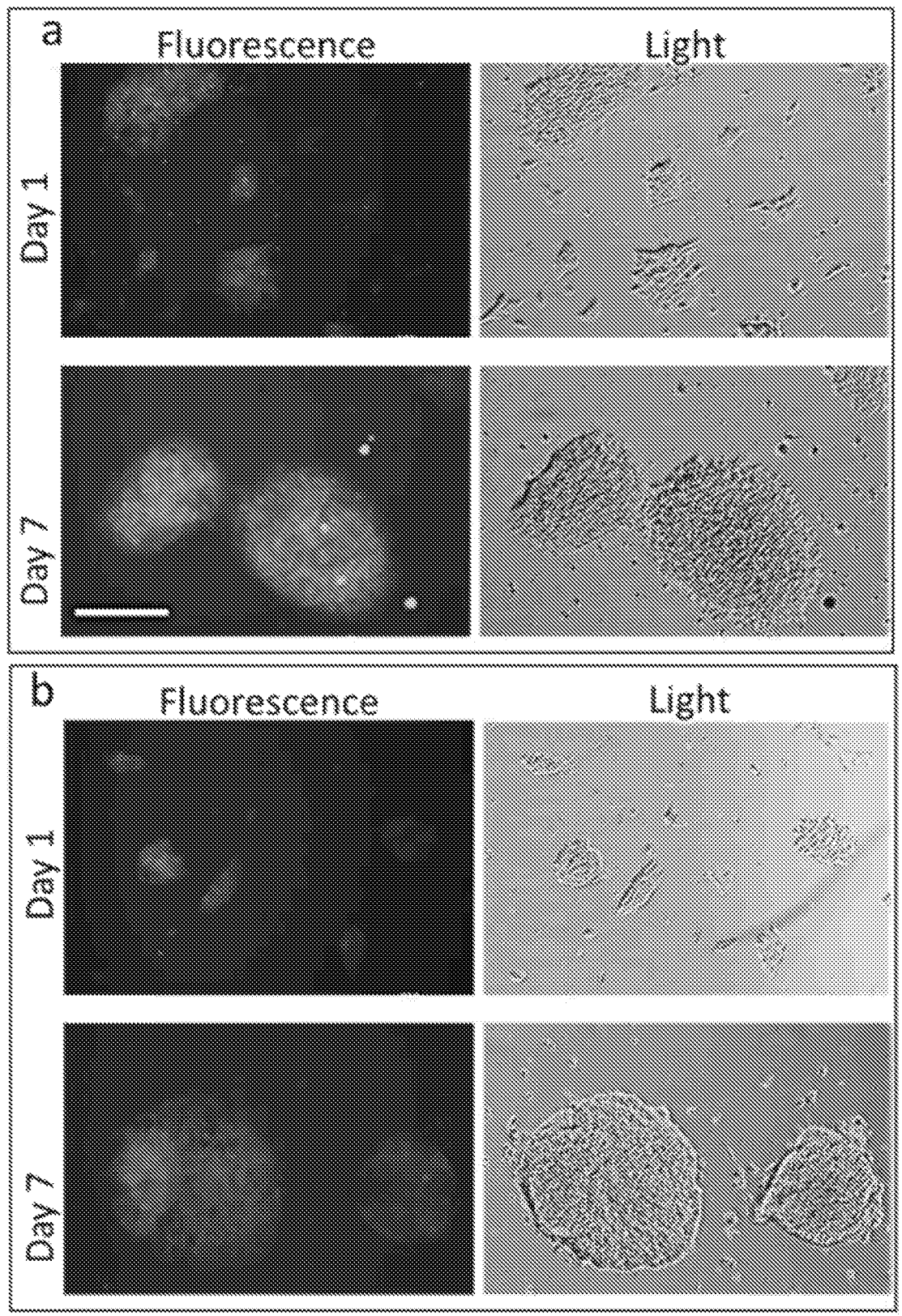

[Fig. 3]
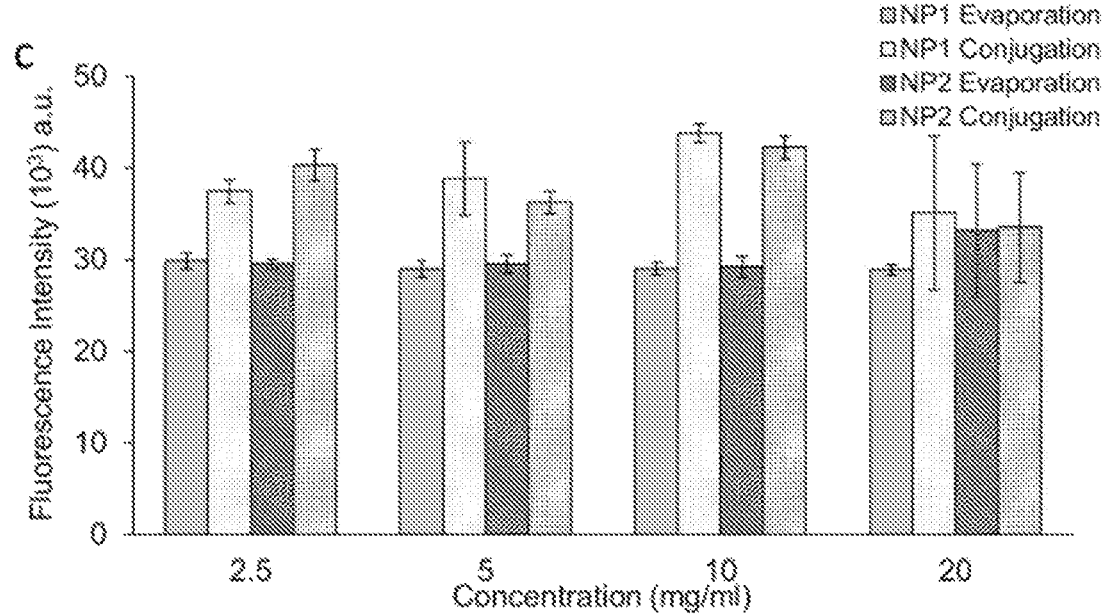
[Fig. 4]
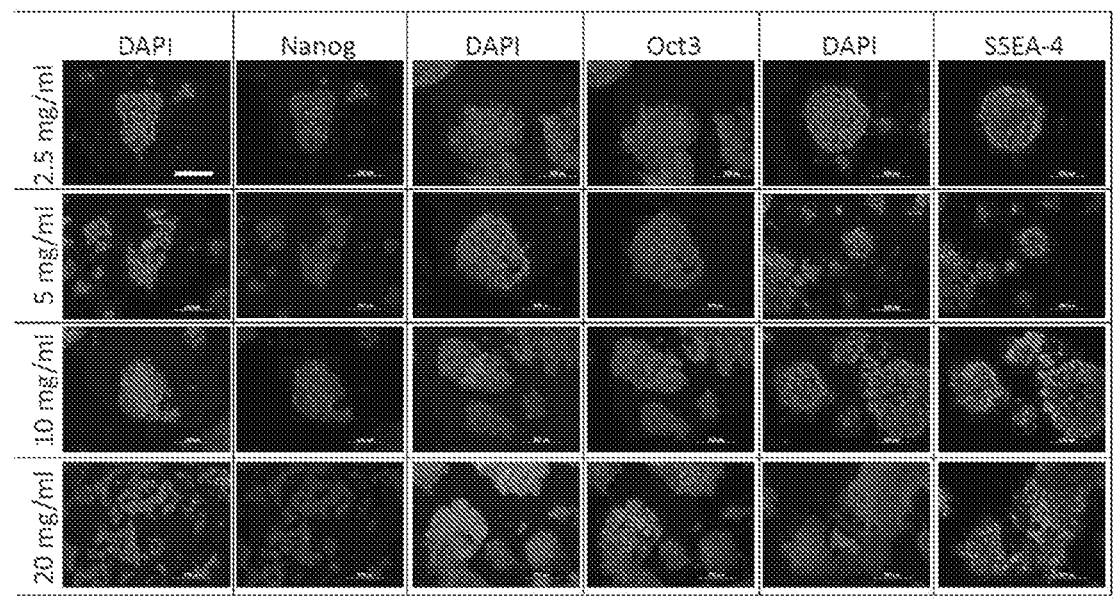

[Fig. 5]
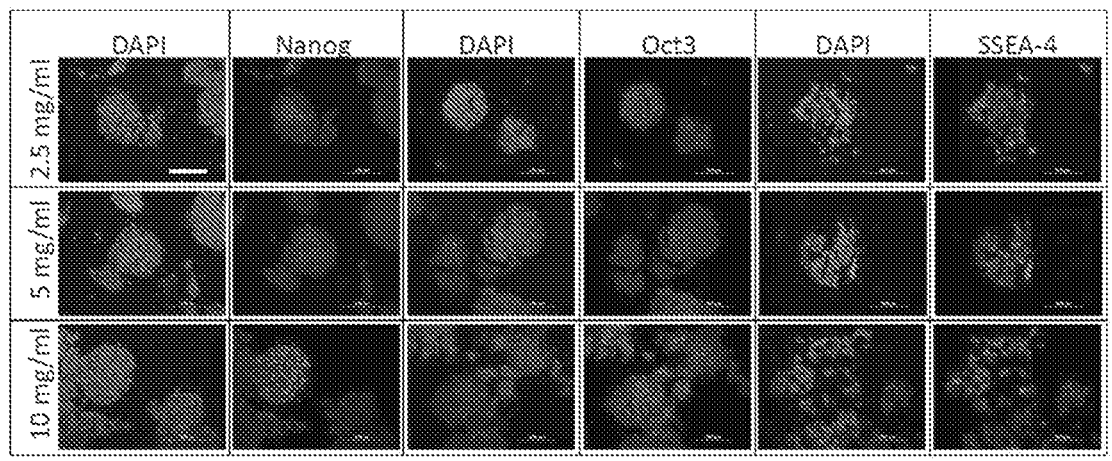
[Fig. 6]
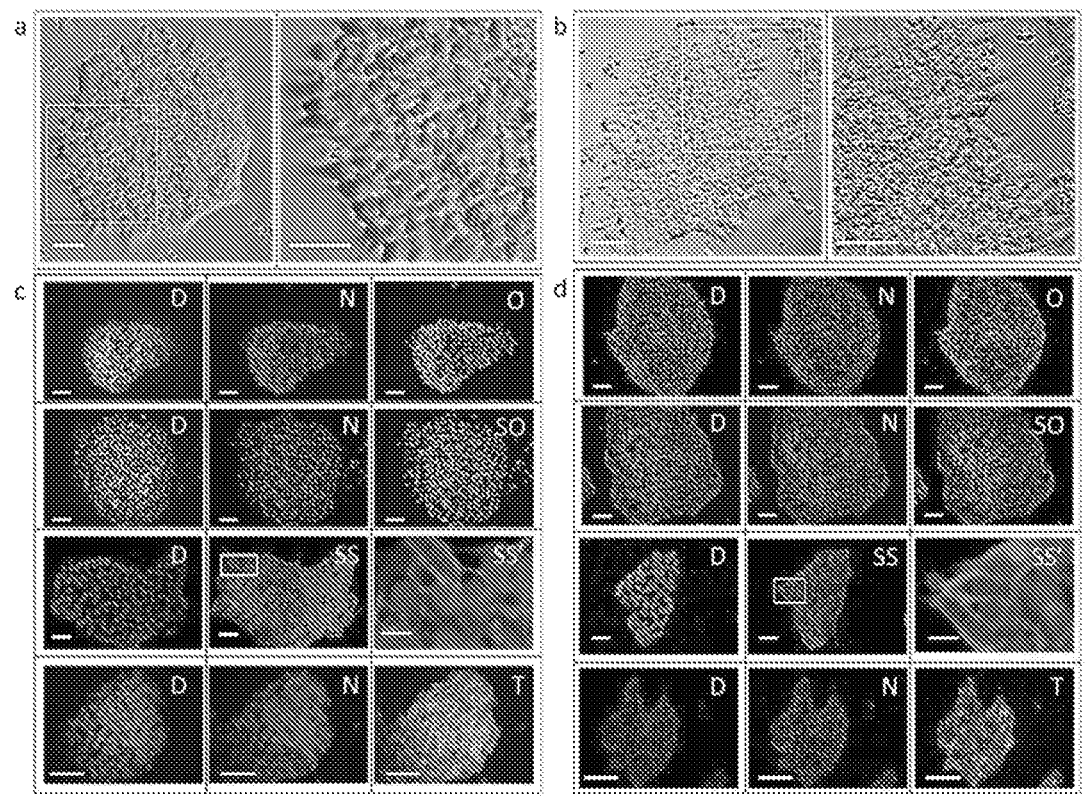

[Fig. 7]
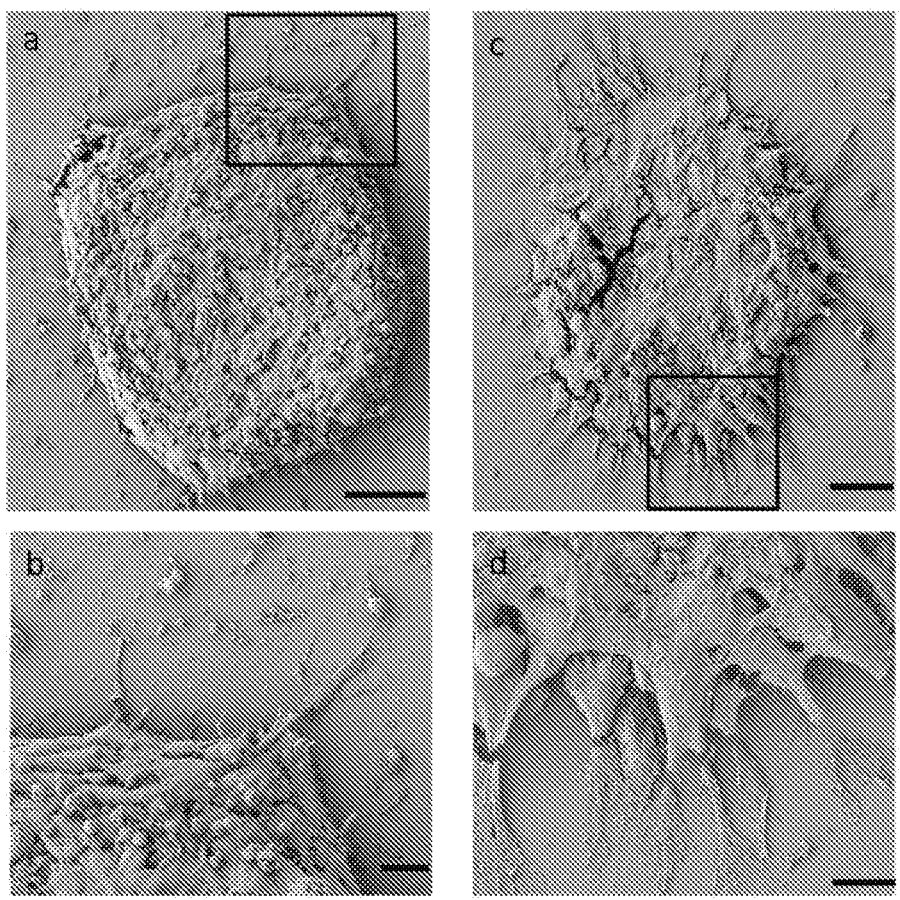

[Fig. 8]
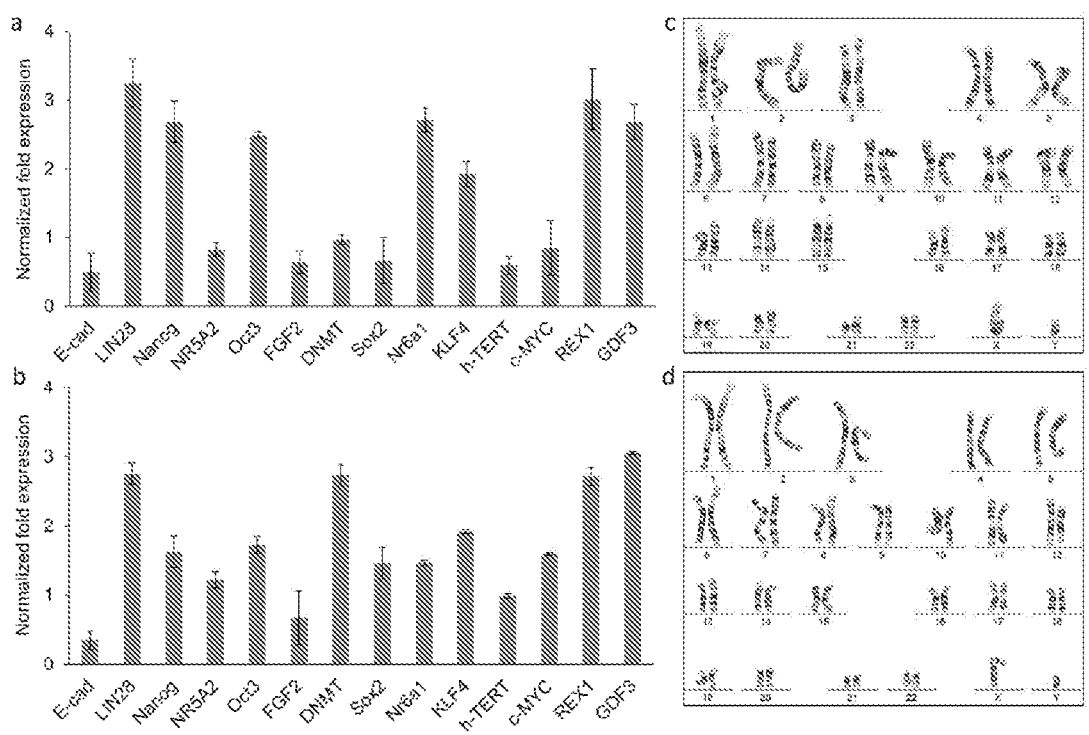

[Fig. 9]
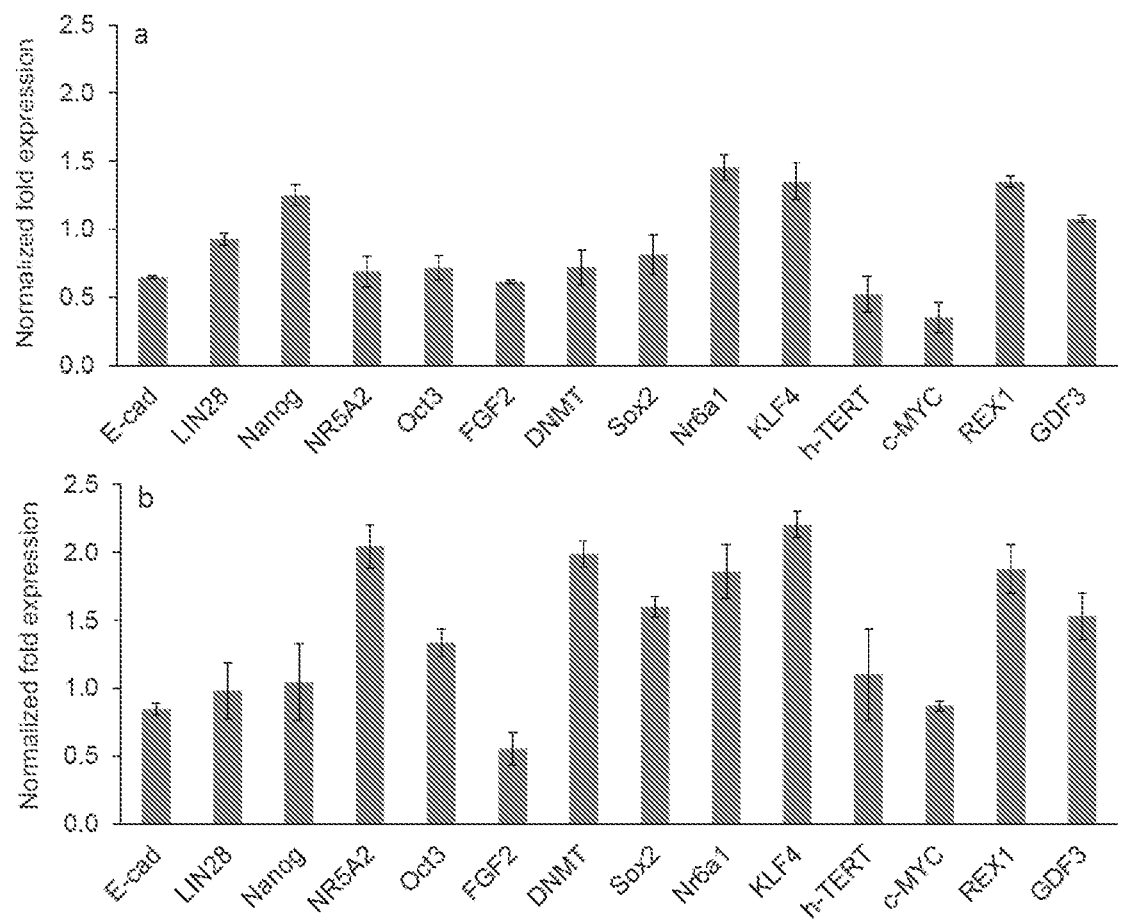

[Fig. 10]
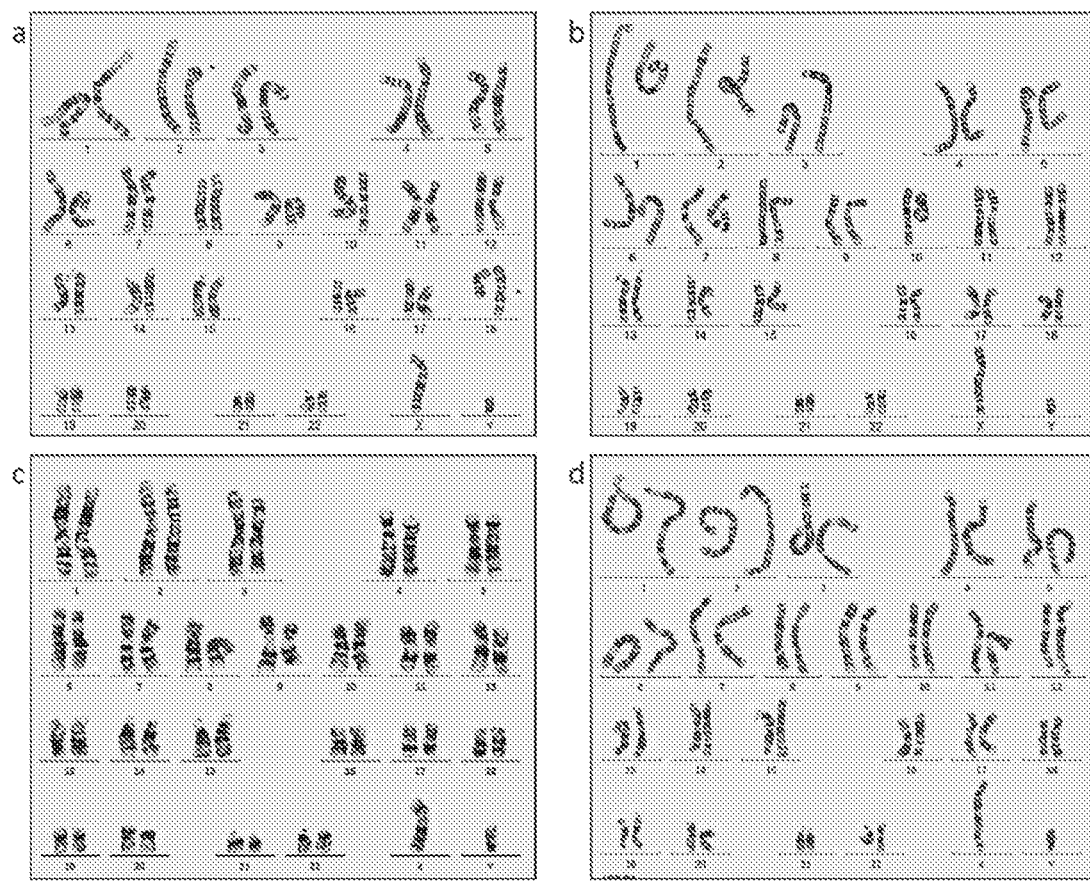

[Fig. 11]
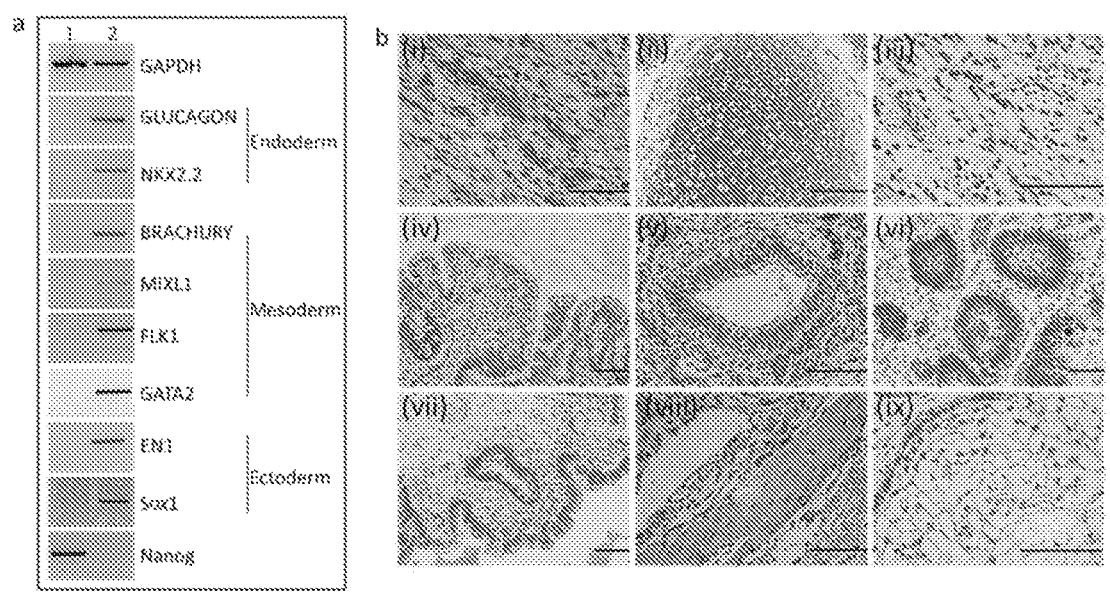
[Fig. 12]
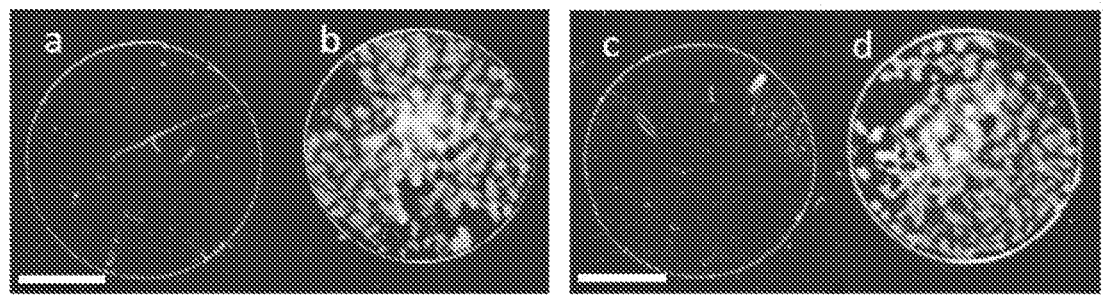

[Fig. 13]
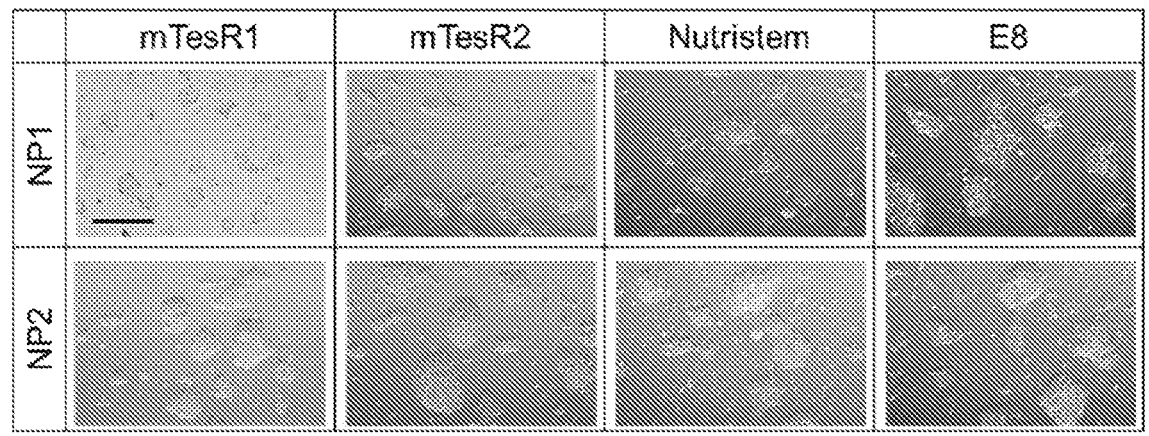
[Fig. 14]
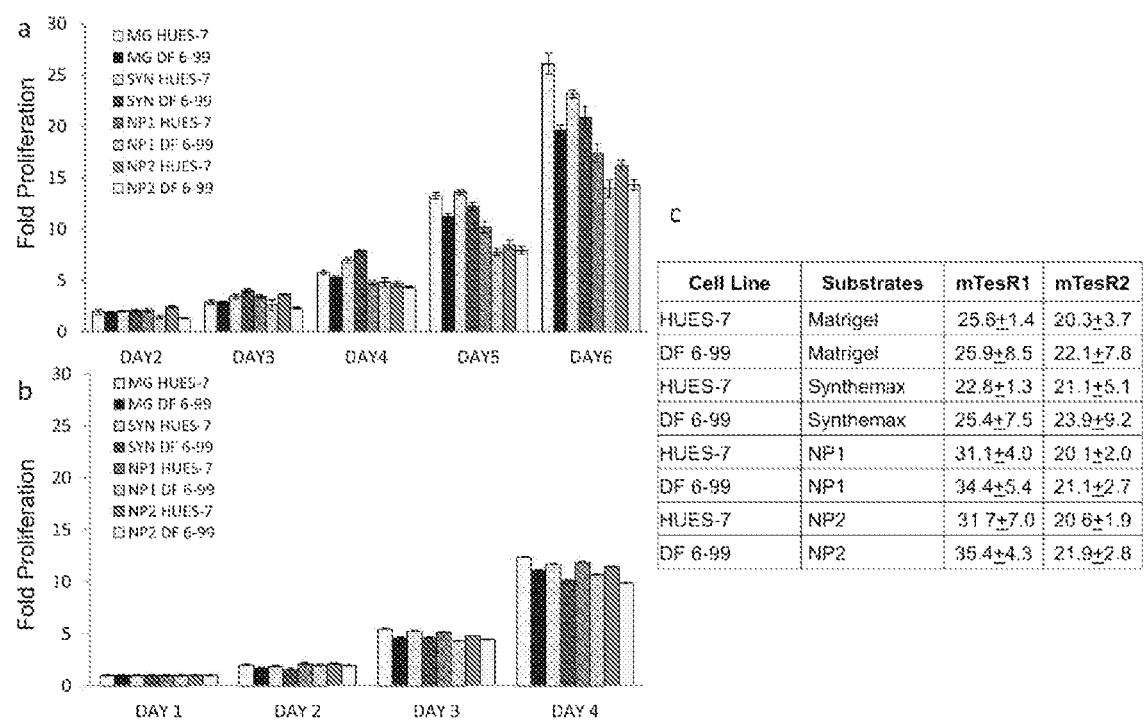

[Fig. 14]
C
| Substrates | Cell Line | mTesR1 | mTesR2 |
|---|---|---|---|
| Matrigel | HUES-7 | 25.6±1.4 | 20.3±3.7 |
| | DF 6-99 | 25.9±8.5 | 22.1±7.8 |
| Synthemax | HUES-7 | 22.8±1.3 | 21.1±5.1 |
| | DF 6-99 | 25.4±7.5 | 23.9±9.2 |
| NP1 | HUES-7 | 31.1±4.0 | 20.1±2.0 |
| | DF 6-99 | 34.4±5.4 | 21.1±2.7 |
| NP2 | HUES-7 | 31.7±7.0 | 20.6±1.9 |
| | DF 6-99 | 35.4±4.3 | 21.9±2.8 |
[Fig. 15]
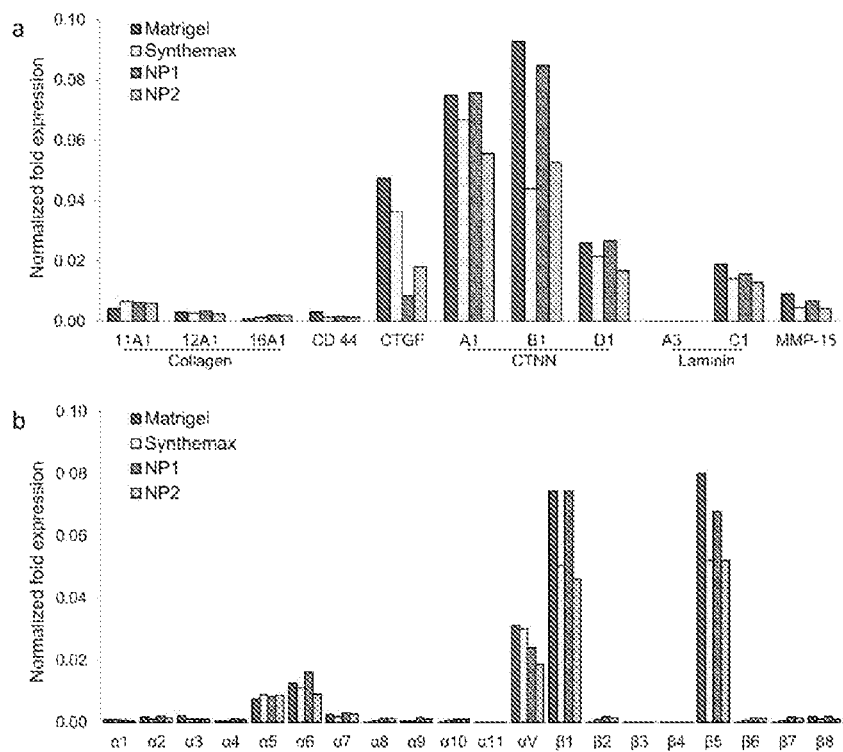

[Fig. 16]
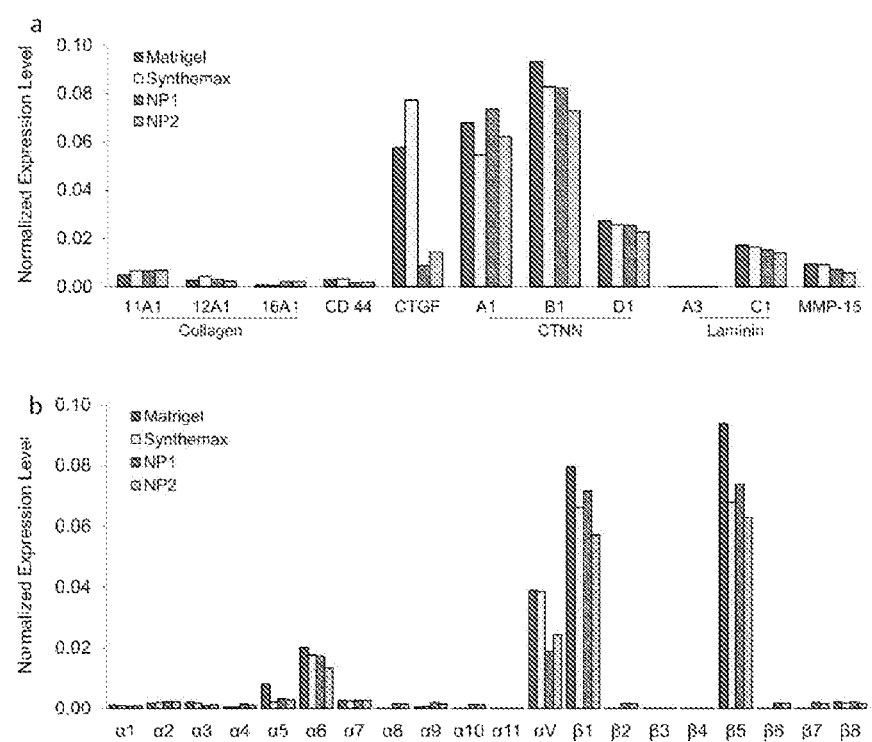

CELL CULTURE SUBSTRATE AND METHOD OF MAKING THEREOF

CROSS-REFERENCE TO RELATED APPLICATIONS

This patent application is a U.S. National Phase application under 35 U.S.C. § 371 of International Application No. PCT/SG2016/050587, filed on 30 Nov. 2016, entitled A CELL CULTURE SUBSTRATE AND METHOD OF MAKING THEREOF, which claims priority to Singapore Patent Application No. 10201509845Q filed 30 Nov. 2015.

TECHNICAL FIELD

The present invention generally relates to a cell culture substrate. The present invention also relates to a method of making the cell culture substrate and a method of culturing stem cells on the cell culture substrate.

BACKGROUND ART

Industrial scale clinical applications of stem cells such as human embryonic stem cells (hESCs) and induced pluripotent stem cells (hiPSCs) in tissue engineering and regenerative medicine require development of well-defined culture conditions for long-term cell propagation. Generally, culture methods for the self-renewal of human embryonic stem cells and induced pluripotent stem cells utilize substrates derived from animal-origin products, which suffer from issues of immunogenicity, high cost, difficulty in isolation and reproducibility.

The development of human embryonic stem cells and induced pluripotent stem cells technology has created enormous potential for regenerative medicine for a number of diseases, such as spinal cord and cardiac injuries, type I diabetes, Parkinson's disease, brain cancer, heart disease, leukaemia, liver disease, motor neurone disease, multiple sclerosis, etc. The application of these cells in tissue engineering remains limited because long-term culture still requires the use of expensive recombinant extracellular matrix (ECM) proteins or animal-derived matrices, which are sources of variability, immunogenicity and xenogenic contamination.

Pluripotent stem cells must self-renew and differentiate when desired, while maintaining an unaltered genome. Although there has been a shift towards the improvement of media formulations and companies are selling more consistent and defined culture media, most systems still involve either undefined or expensive substrates. Hence, to enable clinical and industrial applications of embryonic stem cells, improved, scalable and affordable culture methods are required. A desirable substrate system should provide features such as, controlled cell density and distribution, appropriate chemical, physical and biochemical cues, biocompatibility, non-immunogenicity, reproducibility, and tunable mechanical properties. It should maintain critical cell characteristics such as self-renewal, pluripotency and viability, provide sufficient yields, and be free from pathogens and undefined contaminants.

A commonly used substrate for stem cell culture is Matrigel, which is a gelatinous protein mixture secreted by Engelbreth-Holm-Swarm (EHS) mouse sarcoma cells. As Matrigel resembles the complex extracellular environment found in many tissues, Matrigel is used widely as the substrate of choice for stem cell culture. However, as the composition of Matrigel can vary from lot to lot, experiments that are based on Matrigel may not be reproducible, leading to differing results obtained from different batches. In addition, the animal origin of Matrigel may cause immunogenicity problems when used for human cell therapy, leading to Matrigel being deemed unacceptable for such use.

An alternative to Matrigel are polymeric biomaterials, which have been utilized as substrates for the growth of a variety of cell types. However, approaches using synthetic polymer matrices have sustained only short-term human embryonic stem cells propagation.

There is a need to provide a cell culture substrate that overcomes, or at least ameliorates, one or more of the disadvantages described above.

There is a need to provide a method of making a cell culture substrate that overcomes, or at least ameliorates, one or more of the disadvantages described above.

SUMMARY

According to a first aspect, there is provided a cell culture substrate comprising a substrate having a coating of a plurality of amine functionalized nanoparticles thereon.

Advantageously, the cell culture substrate is a chemically defined synthetic surface and can be used for the sustained propagation of undifferentiated human embryonic stem cells and induced pluripotent stem cells under conditions free from products of animal origin, as well as expensive proteins and peptide materials. Hence, due to the chemical nature of the cell culture substrate, immunogenicity issues associated with animal derived cell culture substrates of the prior art can be effectively minimised or eliminated altogether. The cell culture substrate may thus optionally exclude a coating of peptides or proteins on the surface.

Advantageously, when used to culture human embryonic stem cells, the cell culture substrate may be able to support adhesion and colony formation of more than 90% of the human embryonic stem cells. In addition, the small particle size of the amine functionalized nanoparticles may be able to further improve cell adhesion due to their high surface area and the high number of amine groups that can be presented on the surface of the amine functionalized nanoparticles.

According to a second aspect, there is provided a method of making a cell culture substrate comprising a substrate having a coating of a plurality of amine functionalized nanoparticles thereon, said method comprising the step of spreading said plurality of amine functionalized nanoparticles onto said substrate.

Advantageously, the disclosed method may be simple to use and easy to apply when scaling up. The nanoparticles used in the method may be less expensive than commercially available materials such as Matrigel or Synthemax and can be easily and stably stored at room temperature. The nanoparticles are also free of immunogenicity issues.

According to a third aspect, there is provided a method of culturing stem cells, comprising the step of culturing stem cells in the presence of a culture medium on a cell culture substrate, wherein said cell culture substrate comprises a substrate having a coating of a plurality of amine functionalized nanoparticles thereon.

When the stem cells are cultured on the disclosed cell culture substrate, advantageously, the cell lines (according to the Examples below) may not show any alterations or modifications in their chromosomes after long-term culture on the cell culture substrates.

Further advantageously, the cultured cells may maintain their potential to differentiate into multiple cell types of the three germ layers.

Still advantageously, any differentiated cells may not attach onto the disclosed cell culture substrate while pluripotent colonies attach onto the substrate. Thus, the disclosed cell culture substrate provides an easy way of identifying the pluripotent colonies from the differentiated cells, leading to ease of selecting the pluripotent colonies when required for downstream applications.

Still advantageously, the disclosed cell culture substrates may be used with a variety of culture media and need not be fixed to the use of a particular culture medium.

Still advantageously, the pluripotent stem cells cultured on the disclosed cell culture substrate may retain stable doubling time, typical morphology of human pluripotent stem cells, stem cell marker expression, in vitro and in vivo pluripotency and normal karyotype.

Finally, when cultured on the disclosed cell culture substrate, the cultured stem cells may be serially passaged for at least 10 passages.

Definitions

The following words and terms used herein shall have the meaning indicated:

The term 'amine' is to be interpreted broadly to include the radical $NH_2$.

The term 'alkyl' is to be interpreted broadly to mean straight chain or branched chain saturated aliphatic groups having from 1 to 6 carbon atoms, eg, 1, 2, 3, 4, 5, or 6 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like.

The term "alkoxy" is to be interpreted broadly to mean straight chain or branched alkyloxy groups. Examples include methoxy, ethoxy, n-propoxy, isopropoxy, tert-butoxy, and the like.

The term "heterocycloalkyl" as used herein, includes within its meaning saturated, monocyclic, bicyclic, polycyclic or fused hydrocarbon radicals having from 3 to 10 ring atoms (such as 3, 4, 5, 6, 7, 8, 9 or 10 ring atoms) wherein 1 to 5 ring atoms (such as 1, 2, 3, 4, or 5 ring atoms) are heteroatoms selected from O, N, NH, or S. Examples include isocyanurate, pyrrolidinyl, piperidinyl, quinuclidinyl, azetidinyl, morpholinyl, tetrahydrothiophenyl, tetrahydrofuranyl, tetrahydropyranyl, and the like.

The term "sulfonyl" as used herein, refers to a $—SO_2$ radical.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a cell culture substrate will now be disclosed. The cell culture substrate comprises a substrate having a coating of a plurality of amine functionalized nanoparticles thereon.

The amine functionalized nanoparticles may have a positive charge. The positive charge may be introduced onto the nitrogen atom(s) of the amine group(s) by reacting the nanoparticles with an acid such that the amine functional group(s) on the nanoparticles adopt the positive charge. The charge of the amine functionalized nanoparticles may be determined by obtaining the zeta potential value of the amine functionalized nanoparticles. If the zeta potential value is positive, the amine functionalized nanoparticles are positively charged (conversely, if the zeta potential value is negative, the amine functionalized nanoparticles are negatively charged). The zeta potential value of the positively charged amine functionalized nanoparticles may be more than 0 eV to about +100 eV, such as from more than 0 to about +10 eV, more than 0 to about +20 eV, more than 0 to about +30 eV, more than 0 to about +40 eV, more than 0 to about +50 eV, more than 0 to about +60 eV, more than 0 to about +70 eV, more than 0 to about +80 eV, more than 0 to about +90 eV, more than 0 to about +100 eV, about +10 eV to about +100 eV, about +20 eV to about +100 eV, about +30 eV to about +100 eV, about +40 eV to about +100 eV, about +50 eV to about +100 eV, about +60 eV to about +100 eV, about +70 eV to about +100 eV, about +80 eV to about +100 eV, about +90 eV to about +100 eV, or about +50 eV. By having a positive charge, the positively charged amine functionalized nanoparticles may allow the attachment of cells thereon. The acid used for protonating the amine may be a mineral acid (such as hydrochloric acid, sulphuric acid or phosphoric acid) or an organic acid (such as tartaric acid, succinic acid, maleic acid or citric acid). It is to be appreciated that the choice of a suitable acid for protonation is not limited to those expressly stated but can include any acid that is able to protonate the amine, as is known to a person skilled in the art.

The amine functionalized nanoparticles (which can be neutral or positively charged) may have a particle size in the range of about 50 to about 200 nm, about 50 to about 80 nm, about 50 to about 100 nm, about 50 to about 150 nm, about 80 to about 200 nm, about 100 to about 200 nm, about 150 to about 200 nm, or about 80 to about 110 nm. The particle size may be an average particle size.

The amine functionalized nanoparticles forming the coating may confer a hydrophilic property to the coating. The hydrophilic property of the coating may be determined by obtaining the contact angle of a water droplet when placed on the coating. If the contact angle is less than 90°, the coating is deemed to be hydrophilic. Hence, the contact angle of the coating may be less than about 90°, less than about 60°, less than about 50°, less than about 40°, or less than about 30°.

The concentration of the amine groups on the amine functionalized nanoparticles forming the coating may be measured by X-ray photoelectron spectroscopy and may be in the range of about 0.01 to about 1.0 mM, about 0.01 to about 0.1 mM, about 0.01 to about 0.5 mM, about 0.1 to about 1.0 mM, or about 0.5 to about 1.0 mM.

The amine functionalized nanoparticle may be a polymer of an acrylamide monomer, a cross-linker and an amine monomer. The acrylamide monomer may have the general formula (I)

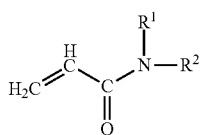

(I)

wherein $R^1$ and $R^2$ is independently hydrogen, an alkyl-amine group having a terminal amine group, or —$C_1$-$C_6$-alkyl optionally substituted with a hydroxyl, a sulphonyl hydroxide, a —$SO_3Na$ group, a carboxylic acid, an amine, or an ammonium ion.

Where $R^1$ or $R^2$ is an alkyl-amine group having a terminal amine group or a $C_1$-$C_6$-alkyl substituted with an amine, the acrylamide monomer may be conjugated to an acid such as a hydrohalic acid (hydrochloric acid, hydrobromic acid or hydroiodic acid).

Hence, the acrylamide monomer may be acrylamide

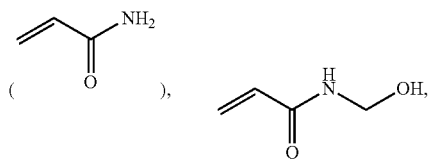

N-aminopropylacrylamide hydrochloride

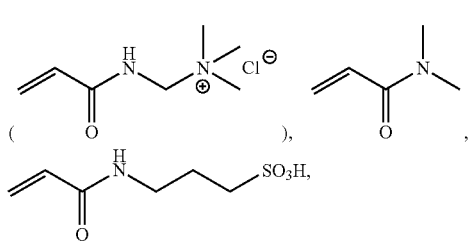

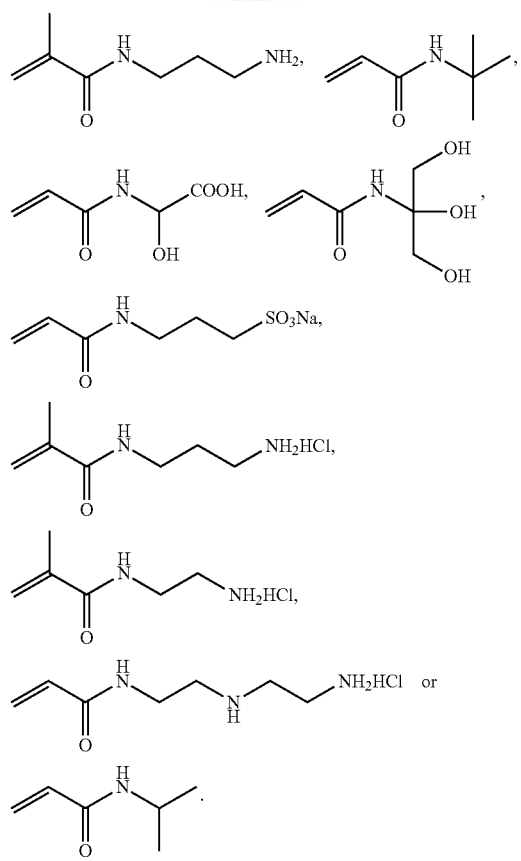

The cross-linker may contain two terminal enone groups, having the general formula (II)

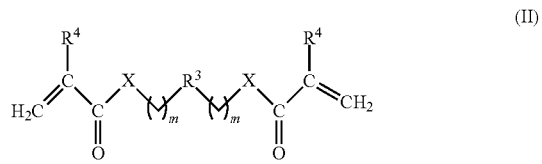

(II)

Wherein m is independently selected from 0 to 6;

X is O or NH;

$R^3$ is an optionally substituted heterocycloalkyl, di-$C_1$-$C_6$-alkoxy-$C_1$-$C_6$-alkyl, —P(O)(OH)— or a —$C_1$-$C_6$-alkyl optionally substituted with a hydroxyl; and $R^4$ is independently hydrogen or —$C_1$-$C_6$-alkyl.

Where $R^3$ is substituted heterocycloalkyl, the heterocycloalkyl may be a 6-membered ring with 3 nitrogen ring atoms. The substituents may be carbonyl and an acrylate, where the carbonyl is bonded to each of the three carbon atoms and the acrylate is bonded to the free nitrogen atom.

Where $R^3$ is di-$C_1$-$C_6$-alkoxy-$C_1$-$C_6$-alkyl, $R^3$ may be [—$CH_2$—O—$CH_2CH_2$—O—$CH_2$-]$_n$, where n is selected from 1 to 25.

Hence, the cross-linker may be N,N'-methylenebisacrylamide

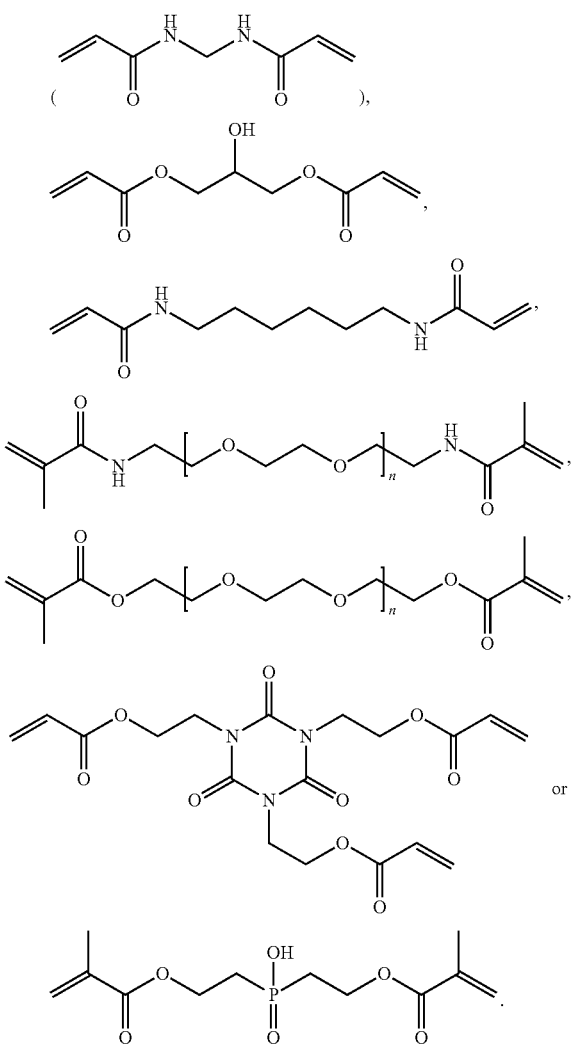

The amine monomer may have the general formula (III)

$$—(CH_2)_y NH_2 \quad \text{(III)}$$

where
y is an integer from 2 to 10 (or 2, 3, 4, 5, 6, 7, 8, 9, or 10).

In particular, the amine monomer may be attached to an acrylamide group and thus may have the formula (IIIa)

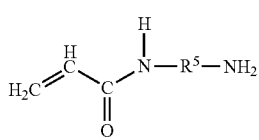

(IIIa)

wherein
$R^5$ is the same as $(CH_2)_y$ mentioned above.

The amine monomer of formula (IIIa) may be conjugated to a hydrohalic acid (such as hydrochloric acid, hydrobromic acid or hydroiodic acid) and hence may have the formula (IIIb) below

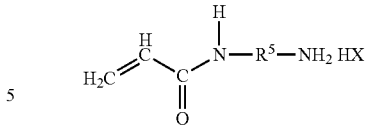

where X is Cl, Br or I.

The polymer may have a molecular weight of about 100 kDa to about 300 kDa, about 150 kDa to about 300 kDa, about 200 kDa to about 300 kDa, about 250 kDa to about 300 kDa, about 100 kDa to about 150 kDa, about 100 kDa to about 200 kDa, or about 100 kDa to about 250 kDa.

The coating on the substrate may be a monolayer of the nanoparticles. Hence, the thickness of the coating on the substrate may be in the same size range as the particle size of the nanoparticles. Hence, the thickness of the coating may have a thickness of about 50 to about 200 nm, about 50 to about 80 nm, about 50 to about 100 nm, about 50 to about 150 nm, about 80 to about 200 nm, about 100 to about 200 nm, about 150 to about 200 nm, or about 80 to about 110 nm.

The substrate may be a silicate substrate, a glass substrate, a tissue culture plate, a plastic substrate, or any surface that can generally be used in cell culture. Where the substrate is a silicate substrate, the silicate substrate may be borosilicate, which is transparent and colourless. The silicate substrate may be aluminosilicate substrate.

Exemplary, non-limiting embodiments of a method of making a cell culture substrate comprising a substrate having a coating of a plurality of amine functionalized nanoparticles thereon will now be disclosed. The method comprises the step of spreading the plurality of amine functionalized nanoparticles onto the substrate.

The cell culture substrate may be one as defined above.

There are provided two methods of making the cell culture substrate, one termed herein as an evaporation method and the other termed herein as the conjugation method.

The evaporation method generally involves spreading a suspension of the amine functionalized nanoparticles (whether neutral or positively charged) on the substrate. The nanoparticles may be suspended in an appropriate fluid medium, such as deionized water, at a concentration of about 2 mg/ml to about 20 mg ml, about 2 mg/ml to about 5 mg ml, about 2 mg/ml to about 10 mg ml, about 2 mg/ml to about 15 mg ml, about 5 mg/ml to about 20 mg ml, about 10 mg/ml to about 20 mg ml, about 15 mg/ml to about 20 mg ml, or about 2 mg/ml to about 10 mg ml. The suspended nanoparticles may be spotted onto the substrate and allowed to spread onto the substrate by gently shaking. The substrate may then be subjected to a step of drying the amine functionalized nanoparticles when spread onto the substrate to obtain a uniform, dry coating.

The conjugation method generally involves introducing complementary functional groups on both the substrate and the amine functionalized nanoparticles to create terminal functional groups that can conjugate or covalently bond with each other. The choice of the functional groups on both the substrate and amine functionalized nanoparticles would be available to a person skilled in the art without undue experimentation. These functional groups can be amine, polyamine, PEGylated amine, carboxyl, thiol, isocyanate, isothiocyanate, urea, etc. As an example, the amine functionalized nanoparticles may be reacted with a thiol containing compound (such as iminothiolane hydrochloride) to form thiol terminal groups on the nanoparticles. The nanoparticles may then be termed as thiol-terminated nanoparticles. The substrate may then be subjected to a step of functionalizing the substrate with a silane containing compound to form terminal functional groups on the surface of the substrate that are capable of forming covalent linkages with the thiol-terminated nanoparticles. Hence, the spreading step comprises the step of reacting the functionalized substrate with the thiol-terminated nanoparticles. The functionalized substrate may be conjugated to the thiol-terminated nanoparticles via covalent bonding or linking. As part of the above example, the substrate may be amine-functionalized with a silanization reagent such as sulfo-succinimidyl-4-[N-maleimidomethyl]cyclohexane-1-carboxylate (sulfo-SMCC) to obtain terminal maleimide groups that then react with the thiol-terminated nanoparticles to obtain covalently linked nanoparticles on the surface of the substrate. The above exemplary reaction is depicted in Scheme 1 below.

Scheme 1

Functionalization of nanoparticle

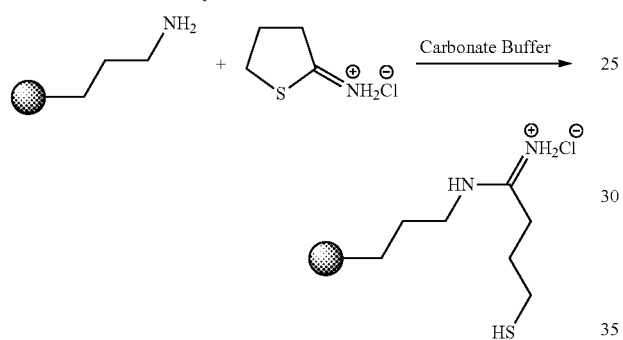

Functionalization of substrate

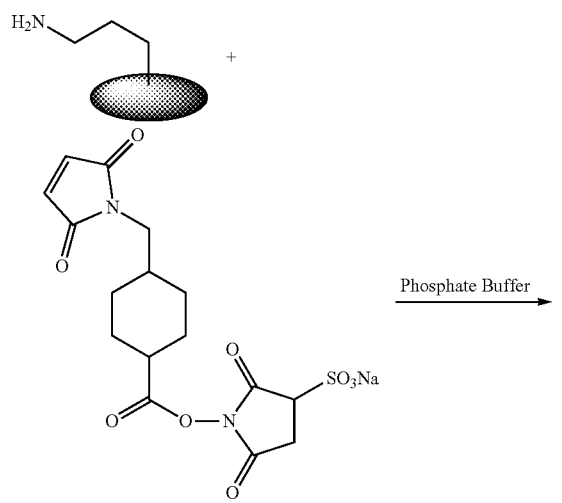

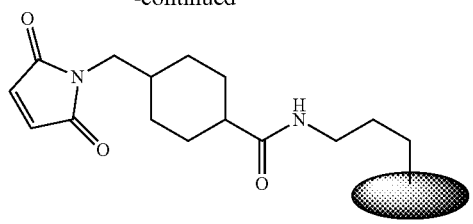

Conjugation of functionalized nanoparticle and functionalized substrate

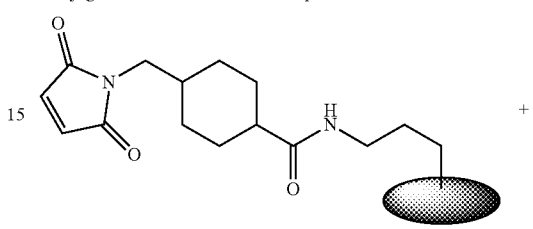

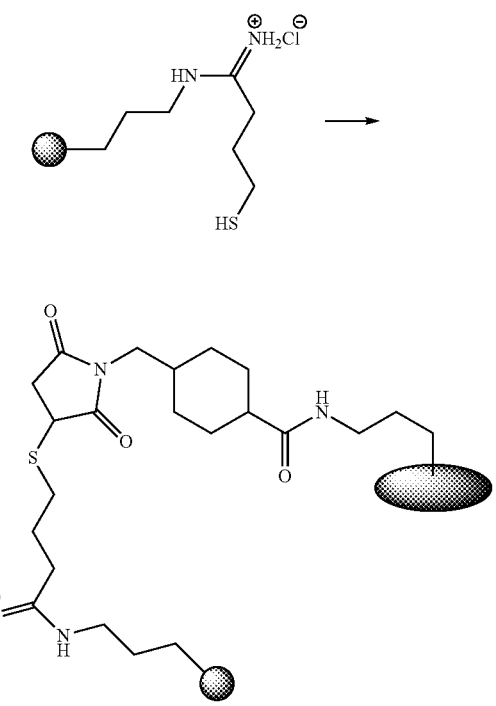

Before reaction with the silanization reagent, the substrate may be cleaned with an organic solvent and dried. The organic solvent may be hexane and ethanol.

Silanes that can be used to functionalize the substrate for covalent conjugation with the nanoparticles may include the following:

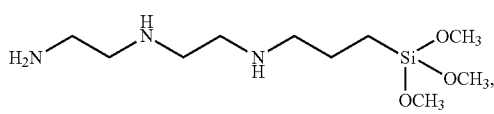

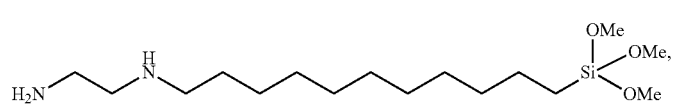

-continued

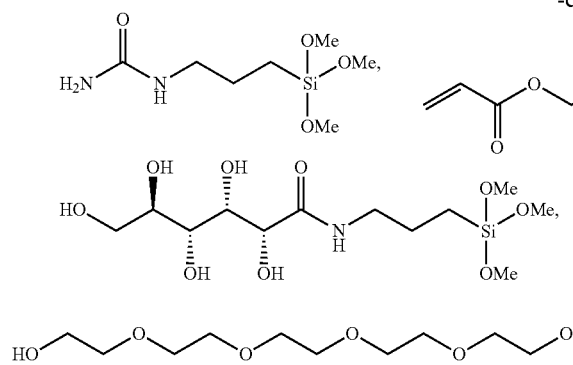
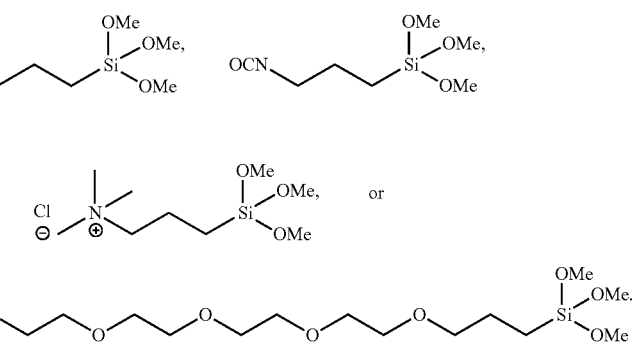

As mentioned above, the amine functionalized nanoparticle may be a polymer of an acrylamide monomer, a cross-linker and an amine monomer. The acrylamide monomer, cross-linker and amine monomer may be as defined above under formulae (I) to (III) respectively. The amine functionalized nanoparticle may be synthesized using a water-in-oil reverse microemulsion method.

Here, the acrylamide monomer, cross-linker and amine monomer may be dissolved in a suitable solvent and if necessary, sonication to ensure complete dissolution. The mixture may be stirred in an inert atmosphere (such as an argon, nitrogen, helium or oxygen-free atmosphere) for a period of time. The mixture may then be mixed with a suitable polymerization initiator for a period of time to ensure complete polymerization. The polymerization may take place in an inert atmosphere such as the one mentioned above, with stirring of the polymerizing mixture so as to obtain uniformly sized nanoparticles, which then may be filtered and washed. If required, the amine functionalized nanoparticles may be crushed and dried in order to dislodge individual nanoparticles from a mass of nanoparticles. When required, the amine functionalized nanoparticles may be stored in an aqueous solution at a low temperature (about 4° C.) for future use.

The concentration of the cross-linker in the amine functionalized nanoparticles may be about 2.5 mol % to about 15 mol %, about 5 mol % to about 15 mol %, about 7.5 mol % to about 15 mol %, about 10 mol % to about 15 mol %, about 12.5 mol % to about 15 mol %, about 2.5 mol % to about 5 mol %, about 2.5 mol % to about 7.5 mol %, about 2.5 mol % to about 10 mol %, or about 2.5 mol % to about 12.5 mol %.

The concentration of the amine monomer in the amine functionalized nanoparticles may be about 2.5 mol % to about 15 mol %, about 5 mol % to about 15 mol %, about 7.5 mol % to about 15 mol %, about 10 mol % to about 15 mol %, about 12.5 mol % to about 15 mol %, about 2.5 mol % to about 5 mol %, about 2.5 mol % to about 7.5 mol %, about 2.5 mol % to about 10 mol %, or about 2.5 mol % to about 12.5 mol %.

Whether evaporation or conjugation is used to coat the amine functionalized nanoparticles on the substrate, the method may further comprise the step of sterilizing the (formed) cell culture substrate. The sterilizing step may include UV irradiation.

The method may further comprise the step of reacting the amine functionalized nanoparticles with an acid to obtain positively charged amine functionalized nanoparticles before coating.

Exemplary, non-limiting embodiments of a method of culturing stem cells will now be disclosed. The method comprises the step of culturing the stem cells in the presence of a culture medium on a cell culture substrate, wherein the cell culture substrate comprises a substrate having a coating of a plurality of amine functionalized nanoparticles thereon.

The cell culture substrate may be one as defined above. The amine functionalized nanoparticles coated on the substrate may have a positive charge.

The stem cell that may be cultured onto the cell culture substrate may be an embryonic stem cell, an induced pluripotent stem cell, a tissue-specific stem cell (adult stem cell), a mesenchymal stem cell, a hematopoietic stem cell, an epidermal stem cell or an epithelial stem cell.

The method may further comprise the step of passaging the cultured stem cells. The passaging step may be repeated for at least 1 passage, at least 5 passages, at least 10 passages or at least 20 passages.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 is a, a schematic diagram showing the synthesis of the amine functionalized nanoparticles.

FIG. 2 shows the characterization of the cell culture substrate (the nanoparticle coated cover slips made in accordance with Example 1 below). a, Field Emission Scanning Electron Microscopy images of a cell culture substrate (i) and (ii) after coating. b, Atomic force microscopy images of (i, iv) uncoated (before coating), (ii, v) NP1- and (iii, vi) NP2-coated cover slips, where (ii, iii) were taken immediately after coating and (iii, vi) were taken after washing the coated covers three times with water. c, X-ray photoelectron spectroscopy analysis of (i) blank, (ii) NP1- and (iii) NP2-coated cover slips. Presence of nitrogen peaks confirms the presence of NP1 and NP2 on the surface.

FIG. 3 shows BG01V/hOG hESCs attachment to nanoparticle-coated coverslips according to Example 2. Fluorescent and light images of BG01V/hOG cells grown on a, NP1 and b, NP2 on day 1 and day 7; the nanoparticles were coated onto the cover slip by deposition via evaporation. On day 7, the cells maintained the green fluorescence and formed cell colonies. Scale bar represents 200 µm. c, Cell attachment measured by plate reader for nanoparticle-coated coverslips. NP1 and NP2 NPs were introduced at the concentrations specified, and coated onto the coverslips via deposition by evaporation or via covalent conjugation.

FIG. 4 shows immunostaining of BG01V/hOG cells cultured for 7 days on cover slip coated with NP1 according to Example 2. NP1 nanoparticles were introduced at the concentrations specified and coated via deposition by evaporation. Antibodies against pluripotent markers Nanog, Oct3 and SSEA-4 were used, and DAPI was employed to stain the nucleus of the cells. Scale bar represents 200 μm.

FIG. 5 shows immunostaining of BG01V/hOG cells cultured for 7 days on cover slip coated with NP2 according to Example 2. NP2 nanoparticles were introduced at the concentrations specified and coated via deposition by evaporation. Antibodies against pluripotent markers Nanog, Oct3 and SSEA-4 were used, and DAPI was employed to stain the nucleus of the cells. Scale bar represents 200 μm.

FIG. 6 shows the characterization of HUES-7 cells grown on nanoparticle surface according to Example 2. Light microscopy images of colonies grown on a, NP1 and b, NP2 coatings. The boxed region of the colony in the left image was shown under higher magnification in the right image to show the details of cell attachment on the NP coatings. Immunostaining of the colonies grown on c, NP1 and d, NP2 coatings at passage 10. The colonies were stained with DAPI (D), and with antibodies against Nanog (N), Oct3 (0), Sox2 (SO), SSEA-4 (SS) and TRA 1-60 (T). The boxed region in SS was shown under higher magnification in SS' to illustrate the membranous location of SSEA-4. Scale bar represents 50 μm, except for SS' (5 μm).

FIG. 7 shows Field Emission Scanning Electron Microscopy images of HUES-7 cells grown on a-b, NP1 and c-d, NP2 coatings according to Example 2. The boxed regions in a and c were shown in higher magnification in b and d, respectively. Scale bar represents 50 μm (a, c) and 10 μm (b, d).

FIG. 8 shows pluripotent gene expression analysis of HUES-7 cells grown for 10 passages on a, NP1 and b, NP2 substrates according to Example 2. The fold difference was calculated with the expression value of cells cultured on Matrigel set as 1 fold. The expression values were normalized with respect to GAPDH. Karyotyping by G-banding of HUES-7 cells grown for 10 passages on c, NP1 and d, NP2 substrates. These cells did not show any chromosomal abnormalities after long-term culture on NP1 and NP2 substrates.

FIG. 9 shows pluripotent gene expression analysis of DF 6-99 cells grown for 10 passages on a, NP1 and b, NP2 substrates according to Example 2. The fold difference was calculated with the expression value of cells cultured on Matrigel set as 1 fold. The expression values were normalized with respect to GAPDH.

FIG. 10 shows karyotyping by G-banding of a-b, H1 and c-d, DF 6-99 cells grown for a b 10, c, 12 and d, 13 passages on a, c, NP1 and b, d, NP2 substrates according to Example 2. These cells did not show any chromosomal abnormalities after long-term culture on NP1 and NP2 substrates.

FIG. 11 shows the differentiation potential of the HUES-7 cells cultured on the synthetic surfaces for 10 passages according to Example 2. a, The differentiation potential of the cells cultured on NP1 surfaces were tested by embryoid body formation assay using a ultra-low attachment plates. PCR analysis indicated that the genes associated with the three germ layers were not detected in the undifferentiated cells (lane 1), while these markers were expressed in the differentiated cells (lane 2). b, The pluripotent stem cells cultured on NP1 were implanted subcutaneously into SCID mice. Formation of teratoma was evident with the histology of the explants. Various tissues such as (i) blood vessels, (ii) cartilage, (iii) neurons, (iv) alveolar epithelium, (v) glandular epithelium, (vi) neuronal rosettes, (vii) skin epithelium, (viii) muscle, and (ix) adipocytes have been identified. Scale bar represents 100 μm.

FIG. 12 shows HUES-7 cells cultured on the cover glasses coated with NP1 and NP2 nanoparticles according to Example 2. Cells grown at a confluent stage were photographed with a Nikon digital camera. Cover glasses with a, b, NP1 coating and c, d, NP2 coating a, c, before seeding the HUES-7 cells, and b, d, after culturing to a confluent stage were shown. Scale bar represents 5 mm.

FIG. 13 shows compatibility of the synthetic nanoparticle surfaces with xeno-free media according to Example 3. Three different commercially available xeno-free media were used in the study, and compared with mTesR1 media. HUES-7 cells were seeded onto the NP1 and NP2 surfaces, and images were taken after 2 days of culture in the respective media. Scale bar represents 200 μm.

FIG. 14 is a comparison of HUES-7 and DF 6-99 proliferation on various surfaces according to Example 3. Pluripotent stem cells were cultured on Matrigel (MG), Synthemax (SYN), NP1 and NP2 surfaces a, with mTesR1 media for 6 days, and b, with mTesR2 media for 4 days. The fold proliferation was obtained from cell counting using a hemocytometer, and the number of cells attached after 24 hours of seeding was taken as 1 fold. c, Doubling time for cell proliferation on different substrates under mTesR1 and mTesR2.

FIG. 15 shows extracellular matrix and integrin subunit gene expression analysis according to Example 4. a, Real-time PCR analysis of the extracellular matrix genes associated with the pluripotency of the stem cells were examined for HUES-7 cells cultured on Matrigel, Synthemax, NP1 and NP2 surfaces. b, Expression profile of various integrin subunits was studied for HUES-7 cells grown on Matrigel, Synthemax, NP1 and NP2 surfaces. The expression levels were normalized against GAPDH and expressed as absolute expression levels.

FIG. 16 shows extracellular matrix and integrin subunit gene expression analyses performed on DF 6-99 cells grown on various substrates according to Example 4. a, Real-time PCR analysis of the ECM genes associated with the pluripotency of the stem cells were examined for DF 6-99 cells cultured on Matrigel, Synthemax, NP1 and NP2 surfaces. b, Expression profile of various integrin subunits was studied for DF 6-99 cells grown on Matrigel, Synthemax, NP1 and NP2 surfaces. The expression levels were normalized against GAPDH and expressed as absolute expression levels.

EXAMPLES

Non-limiting examples of the invention will be further described in greater detail by reference to specific Examples, which should not be construed as in any way limiting the scope of the invention.

All chemicals, surfactants, reagents and solvents were purchased from Sigma-Aldrich (Missouri of the United States of America) or Polysciences Inc (from Pennsylvania of the United States of America) and used without further purification.

Example 1

General Synthesis of Nanoparticles

Nanoparticles were synthesized by a water-in-oil reverse microemulsion method based on FIG. 1a. Typically, the monomer (16 mmol), crosslinker (1.6 mmol, 10 mol % crosslinking) and the amine-terminated monomer (1.6 mmol, 10 mol %) as mentioned above were dissolved in phosphate buffer (4 mL, 10 mM, pH 7.2) by sonication for 2 minutes to obtain a clear solution. The resulting monomer solution was added to a 250-mL round-bottom flask containing an argon-purged, well-stirred solution of dioctyl sulfosuccinate (AOT or Aerosol AT (3.2 g) and Brij 30 (6.4 mL) in hexanes (100 mL). The mixture was stirred under an argon blanket at room temperature for 10 minutes. The reaction mixture was treated with freshly prepared aqueous ammonium persulfate (65 µL, 10%) and N,N,N',N'-tetramethylethylenediamine (TEMED) (85 µL) to initiate polymerization, and stirred further at room temperature (or about 20° C.) overnight under argon to ensure complete polymerization. The hexane solvent was evaporated under reduced pressure to obtain a thick residue, which was suspended in absolute ethanol (100 mL) by sonication. The precipitated particles were filtered and thoroughly washed with ethanol (10×100 mL) in an Amicon stirred cell equipped with a Millipore cellulose filter membrane (100 kDa, filtration pressure=1.5 bar nitrogen). The solid material was gently crushed into a fine powder and subjected to air drying. The product was suspended in water (20 mg/mL) and sonicated to obtain a homogeneous solution, filtered through 0.45-mM filter, and purified by ultrafiltration using Millipore cellulose filter (100 kDa) and water (10×50 mL). The concentrated sample was made into an aqueous solution (20 mg/mL) and stored at 4° C. until further use.

Coating of Nanoparticles on the Cover Slips by Evaporation

The purified nanoparticles were suspended in deionized water in appropriate concentrations, and the desired volume (100 L) was spotted on the cover slips placed in a 24-well tissue culture plate. The solution was spread uniformly over the cover slips by gentle shaking, and was dried under air or at 50° C. until a uniform, dry layer was obtained. The coated cover slips were directly used for stem cell culture after sterilization with UV irradiation.

Coating of Nanoparticles on the Cover Slips by Covalent Linkage

The cover slips were washed thoroughly with hexane and ethanol and dried. The surface of cover slips was functionalized with silanization using the appropriate functionalized trimethoxysilyl reagent in dry methanol or heptane to obtain the reactive surface groups such as amine, polyamine, PEGylated amine, carboxyl, thiol, isocyanate, isothiocyanate, urea, etc. For example, amine-functionalized cover slips were reacted with sulfo-succinimidyl-4-[N-maleimidomethyl]cyclohexane-1-carboxylate (sulfo-SMCC) to obtain terminal maleimide groups. In parallel, the amine-functionalized NPs were reacted with iminothiolane hydrochloride to obtain a thiol derivative. The thiol-terminated nanoparticles were reacted with maleimide-functionalized cover slips to obtain the covalently linked nanoparticles on the surface via maleimide chemistry. These cover slips were sterilized under UV irradiation and directly used for stem cell culture.

In terms of supporting the self-renewal of stem cells, the coating of cover slips by nanoparticles achieved via evaporation was as excellent as that obtained via covalent conjugation. The former obviously presented a major advantage of simplicity and practicality giving its ease of application with a suspension of nanoparticles. In addition, the polymeric nanoparticulate suspension would be much less expensive than commercially available materials (such as Matrigel and Synthemax), can be easily and stably stored at room temperature, and is free of immunogenicity issues.

Tables 1 to 3 below show the synthesis of nanoparticles of various compositions and with varying amounts of components.

TABLE 1

Synthesis of nanoparticles of various compositions and different methods showing particle size, zeta potential and contact angle

| Monomer | Cross-Linker | Functional Group (10%) | Size (nm) | Zeta Potential (eV) | Contact Angle (°) | Evaporation Conjugation | Attachment |
|---|---|---|---|---|---|---|---|
| Acrylamide (CH2=CH-C(O)-NH2) | N,N'-methylenebisacrylamide | — | 102 | −2 | 52 | Evaporation | No |
| Acrylamide (CH2=CH-C(O)-NH2) | N,N'-methylenebisacrylamide | —(CH$_2$)$_3$NH$_2$ | 88 | +88 | 38 | Both | Yes (NP1) |
| Acrylamide (CH2=CH-C(O)-NH2) | N,N'-methylenebisacrylamide | —(CH$_2$)$_3$NH$_3$Cl | 106 | +96 | 24 | Both | Yes (NP2) |
| Acrylamide (CH2=CH-C(O)-NH2) | Glycerol diacrylate (bis-acrylate with OH) | —(CH$_2$)$_3$NH$_2$ | 150 | +65 | 41 | Both | Yes |

TABLE 1-continued

Synthesis of nanoparticles of various compositions and different methods showing particle size, zeta potential and contact angle

| Monomer | Cross-Linker | Functional Group (10%) | Size (nm) | Zeta Potential (eV) | Contact Angle (°) | Evaporation Conjugation | Attachment |
|---|---|---|---|---|---|---|---|
|  | 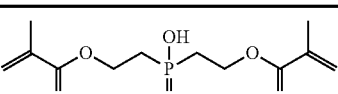 | —(CH$_2$)$_3$NH$_2$ | 104 | −4 | 43 | Both | No |
| 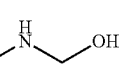 | 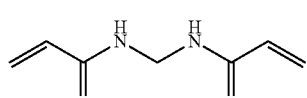 | —(CH$_2$)$_3$NH$_2$ | 91 | +38 | 51 | Both | Partial, after 2 days |
| 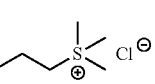 | 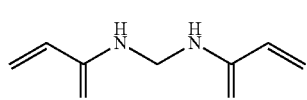 | —(CH$_2$)$_3$NH$_2$ | 79 | +88 | 21 | Both | Partial, after 2 days |
|  | 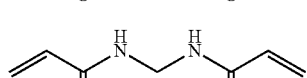 | —(CH$_2$)$_3$NH$_2$ | 102 | +44 | 54 | Both | Partial |
|  | 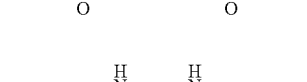 | —(CH$_2$)$_3$NH$_2$ | 109 | −5 | 34 | Both | No |
|  |  | —(CH$_2$)$_3$NH$_2$ | 137 | +46 | 36 | Both | Partial |

Dynamic light scattering (DLS) showed that NP1 and NP2 have an average size of 88 nm and 150 nm, respectively, and a zeta potential of +88 and +65 mV, respectively (Table 1). The purified nanoparticles (20 mg/mL) were suspended in deionized water and coated on the cover slips by evaporation. The NP1 and NP2 coatings were hydrophilic, with a contact angle of 38° and 24° respectively (Table 1). Nanoparticles NP1 and NP2 were then selected for further experiments.

TABLE 2

Effect of amine concentration in nanoparticle synthesis

| Monomer | Cross-Linker (10%) | —(CH$_2$)$_3$NH$_2$ Functional Group (%) | Evaporation/ Conjugation | Attachment |
|---|---|---|---|---|
| 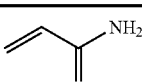 | 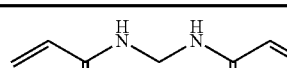 | 0 | Evaporation | No |
| 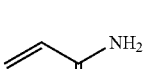 |  | 2.5 | Both | Yes |
| 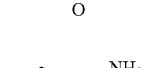 |  | 5 | Both | Yes |

TABLE 2-continued

Effect of amine concentration in nanoparticle synthesis

| Monomer | Cross-Linker (10%) | —(CH$_2$)$_3$NH$_2$ Functional Group (%) | Evaporation/ Conjugation | Attachment |
|---|---|---|---|---|
| acrylamide | N,N'-methylenebisacrylamide | 10 | Both | Yes |
| acrylamide | N,N'-methylenebisacrylamide | 25 | Both | Yes |
| acrylamide | N,N'-methylenebisacrylamide | 50 | Both | Yes |
| acrylamide | N,N'-methylenebisacrylamide | 75 | Both | Yes |
| acrylamide | N,N'-methylenebisacrylamide | 100 | Both | Yes |

From Table 2, it can be seen that having the amine functional group is essential to obtaining attachment of the cells on the cell culture substrate.

TABLE 3

Effect of cross-linkers in nanoparticle synthesis

| Monomer | Cross-linker | Cross-Linker (%) | —(CH$_2$)$_x$NH$_2$ (x = 2, 3) Functional Group (%) | Evaporation/ Conjugation | Attachment |
|---|---|---|---|---|---|
| acrylamide | N,N'-methylenebisacrylamide | 10 | 0 | Evaporation | No |
| acrylamide | N,N'-methylenebisacrylamide | 10 | 10 | Both | Yes |
| acrylamide | glycerol diacrylate | 10 | 10 | Both | Yes |
| acrylamide | bis(methacryloyloxyethyl) phosphate | 10 | 10 | Both | No |
| acrylamide | N,N'-methylenebisacrylamide | 5 | 10 | Both | Yes |

TABLE 3-continued

Effect of cross-linkers in nanoparticle synthesis

| Monomer | Cross-linker | Cross-Linker (%) | —(CH$_2$)xNH$_2$ (x = 2, 3) Functional Group (%) | Evaporation/ Conjugation | Attachment |
|---|---|---|---|---|---|
| acrylamide | N,N'-methylenebisacrylamide | 25 | 10 | Both | Yes |
| acrylamide | N,N'-methylenebisacrylamide | 50 | 10 | Both | Yes |
| acrylamide | bis(2-methacryloyloxyethyl) phosphate | 5 | 10 | Both | Yes, Gel Formation |
| acrylamide | bis(2-methacryloyloxyethyl) phosphate | 5 | 25 | Both | Yes, Gel Formation |

From Table 3, it can be seen that having the amine functional group is essential to obtaining attachment of the cells on the cell culture substrate. In addition, where the cross-linker is negatively charged, having an excess of the amine functional group may aid in attachment.

Characterizations of Nanoparticle Coated Cover Slips

Nanoparticle coated cover slips were characterized as-coated and after they were washed three times with water.

Field Emission Scanning Electron Microscope (FESEM) was conducted with JEOL JSM-7400F. The coverslips were frozen in liquid nitrogen prior to freeze drying to keep the sample's morphology intact. The coverslips were mounted on metal holders and vacuum coated with a platinum layer before FESEM studies. The FESEM images are shown in FIG. 2a where both (i) and (ii) are the images after coating, except that (i) was obtained at low resolution and (ii) was obtained at high resolution. The scale bar of (i) is at ×25 magnification while that for (ii) is at ×30,000 magnification.

Atomic Force Microscopy (AFM) was performed using a tapping mode on a Veeco Multimode AFM AS-12V Scanner with a Bruker RTESPA tip. The coverslips were mounted on metal holders. The center of the coverslips was examined over a length and width of 1-10 μm at a scan rate of 1 Hz. The AFM images are shown in FIG. 2b whereby the surface morphology of the coated cover slips before and after washing with deionized water three times were illustrated. It can be seen that a thin, uniform layer of nanoparticles was achieved on the cover slips after washing.

Theta Probe X-ray Photoelectron Spectroscopy (XPS) was used with monochromatic Al Kα X-rays (hu=1486.6 eV) at an incident angle of 30° with respect to surface normal. Photoelectronswere collected at a take-off angle of 50° with respect to surface normal. The analysis area was about 400 μm in diameter, and the maximum analysis depth was 4 to 10 nm. The XPS analysis is shown in FIG. 2c which confirmed the presence of nitrogen-containing surface species associated with the amine functionalized nanoparticles.

Example 2

Cell Culture

The tested cell culture substrates (such as the nanoparticle coated cover slips) were washed twice with Dulbecco's phosphate-buffered saline (DPBS, obtained from Invitrogen of California of the United States of America). The washed cover slips were placed in 24-well plates, and BG01V/hOG and HUES-7 cells were seeded and cultured for 48 hours in serum-free defined media mTesR1 (from Stem Cell Technologies of Singapore). BG01V/hOG was obtained from LifeTechnologies (California of the United States of America). HUES-7 cell line was obtained from Harvard University (Massachusetts of the United States of America). mTesR1 was prepared by mixing the supplements with basal media and the complete media was aliquoted in 50-mL tubes for regular use.

Matrigel-coated 24-well plates (obtained from BD Biosciences, of New Jersey of the United States of America) and Synthemax plates (obtained from Corning of New York of the United States of America) were used as positive controls. Media was changed every 24 hours and monitored for unwanted differentiation of the cell colonies. The cells grown on the nanoparticle-coated glass cover slips became confluent in 6 to 7 days, and passaged subsequently onto similar nanoparticle-coated cover slips at 1:3 ratio using dispase. Here, the cells grown to confluence on the substrates were gently rinsed twice with knockout Dulbecco's medium (DMEM). Dispase was added to the cells, and incubated at 37° C. for 6 minutes. The cells were further rinsed twice with knockout DMEM. The pluripotent stem colonies were dislodged with a cell scraper, and seeded onto a new substrate at a dilution of 1:5.

The free amine groups on the nanoparticles were made positively charged by treating with dilute hydrochloric acid (1 N) (NP2). Nanoparticles with free amine groups (NP1)

and positive charge (NP2) showed similar behavior in cell adhesion and propagation (FIG. 3).

Pluripotency

Initial screening of the materials suitable for the stem cell attachment was conducted with BG01V/hOG cells, which express EmGFP (Emerald Green Flurorescent Protein) under the control of human Oct4 promoter. The expression of GFP is an indication that these cells maintain their pluripotency during culture. FIG. 3a shows that the cells cultured for 1 day and for 7 days on NP1 coating maintained the GFP expression. Moreover, the cells were observed to grow in colonies under light microscope. Similar results were observed for NP2 coating (FIG. 3b).

The measured fluorescence intensity of the cells indicated that the cell attachment was not substantially affected by the nanoparticle concentration introduced or the method of nanoparticle coating (FIG. 3c) Immunostaining with antibodies also confirmed that the cells maintained their pluripotency at Day 7, regardless of the nanoparticle concentration used for both NP1 and NP2 coatings (FIG. 4 and FIG. 5 respectively). This suggested that a thin layer of nanoparticle coating on the glass surface was sufficient to support the attachment and proliferation of hESCs. Excess nanoparticles were found to disintegrate, and could be effectively washed away by water prior to cell seeding.

Apart from the GFP-tagged hESCs, some of the common hESC lines (HUES-7, H1 and H7) and hiPSC lines (hFib2-iPS4 and DF 6-99) have also been examined. H1, H7 and DF 6-99 were purchased from WiCell Research Institute (Wisconsin of the United States of America). HUES-7 was investigated for long-term culture on the nanoparticle surface. The pluripotent stem cell attachment, cell doubling time, viability, colony morphology and pluripotency status were studied at the end of each passage. Light microscopy showed that the colonies adhered to the nanoparticle surfaces with a firm binding. Higher magnification images further illustrated the cellular processes for the cells that were present on the outer ring of the colony (FIG. 6a and FIG. 6b). This was further supported by FESEM images of the colonies (FIG. 7) Immunostaining with antibodies against Nanog, Oct3, Sox2, SSEA-4 and TRA 1-60 showed that the cells grown on NP1 and NP2 coatings for up to 10 passages maintained their pluripotency (FIG. 6c and FIG. 6d). Furthermore, flow cytometry results with pluripotent markers indicated that the cells cultured on NP1 and NP2 substrates were 98% positive for Nanog, Oct3, Sox2 and TRA 1-60 markers (Table 4). Fluorescence-activated cell sorting (FACS) with SSEA-4 antibody showed 71% and 70% positive cells for NP1 and NP2 substrates, respectively. It was remarkable that the percentage of cells that stained positive for the various pluripotent markers were either comparable to or higher than that achieved for Matrigel and Synthemax substrates under similar culture conditions.

TABLE 4

Comparison of pluripotency by flow cytometry. The percentages of positively labeled cells are indicated in the table.

| Substrate | Nanog | Oct3 | Sox2 | TRA 1-60 | SSEA-4 |
|---|---|---|---|---|---|
| Synthemax | 79 | 68 | 79 | 61 | 76 |
| Matrigel | 98 | 86 | 92 | 75 | 72 |
| NP1 | 99 | 98 | 99 | 98 | 71 |
| NP2 | 99 | 98 | 99 | 98 | 70 |

Other cell lines (such as H1, H7 and DF 6-99 cells) cultured for 10 passages on NP1 and NP2 substrates showed similarly excellent pluripotency by FACS (Table 5).

TABLE 5

H1, H7 and DF 6-99 cells were cultured for 10 passages on NP1 and NP2 surfaces. The percentage of cells detected positive for each antibody was tabulated.

| Cell Line | Substrate | Nanog | Oct3 | SSEA-4 |
|---|---|---|---|---|
| H1 | NP1 | 99 | 99 | 91 |
|  | NP2 | 99 | 100 | 95 |
| H7 | NP1 | 100 | 100 | 93 |
|  | NP2 | 100 | 100 | 93 |
| DF 6-99 | NP1 | 95 | 99 | 86 |
|  | NP2 | 100 | 99 | 68 |

The culture of HUES-7 cells on NP1 and NP2 were continued for up to 23 passages, and it was found that the pluripotency was not compromised on these nanoparticle substrates. At 23 passages, the cells grown on NP1 and NP2 were 94 to 98% positive for Oct3 and Nanog, and 73 to 83% positive for TRA 1-60 (Table 6). These results clearly illustrated that the stem cells maintained their pluripotency during the long-term culture on the NP surfaces.

TABLE 6

HUES-7 cells were cultured for 23 passages on NP1 and NP2 surfaces. The percentage of cells detected positive for each antibody was tabulated.

| Substrate | Nanog | Oct3 | TRA 1-60 |
|---|---|---|---|
| NP1 | 94 | 98 | 73 |
| NP2 | 97 | 96 | 83 |

The gene expression profiles of pluripotent markers such as Oct3, SSEA-4 and Nanog were analyzed for HUES-7 cells grown on Matrigel and nanoparticle surfaces (FIG. 8a and FIG. 8b). For the nanoparticle surfaces, majority of the 14 genes showed an expression level similar to or higher than those for Matrigel. In particular, expression of Lin28 increased by about 3 folds on NP1 and NP2 substrates. Lin28 expression in hiPSC line DF 6-99 grown on nanoparticle surfaces remained similar to that on Matrigel. A consistent increase in the expressions of KLF4, REX1 and GDF3 in HUES7 and DF 6-99 cells on nanoparticle surfaces was also noticed at passage 10 (FIG. 8a, FIG. 8b and FIG. 9). On the other hand, expression of E-cadherin (E-cad) in HUES-7 and DF 6-99 cells grown on nanoparticle surfaces was noticed to be lower than that on Matrigel.

Determination of Chromosomal Abnormalities

Pluripotent stem cells are highly susceptible to chromosomal abnormalities depending on the culture conditions. To determine if any chromosomal abnormalities were introduced by the culture conditions, karyotyping of HUES-7, H1 and DF 6-99 cells that were cultured for ≥10 passages on nanoparticle surfaces was performed. These hESC and iPSC cell lines showed no alterations or modifications in their chromosomes after long-term culture on NP1 and NP2 substrates (FIG. 8c, FIG. 8d and FIG. 10). For long-term culture, the cells were continuously cultured and subcultured onto the specific substrate for at least 10 passages. Typically, each passage was done at day 7 of the culture.

Differentiation Potential

The differentiation potential of the pluripotent stem cells that were cultured for 10 passages on NP1 were tested via embryoid body (EB) formation assay. The differentiated EBs were examined for the expression of the three germ layers, i.e. endoderm, mesoderm and ectoderm specific markers by polymerase chain reaction (PCR) using gene-specific primers (FIG. 11a). Additionally, the differentiation potential was tested by in vivo teratoma assay. When subcutaneously implanted into immunocompromised mice, the passage-10 cells that were grown on NP1 developed into a teratoma that contained cell types of the three germ layers (FIG. 11b). Results obtained from the EB formation assay and teratoma assay illustrated that the cells maintained their potential to differentiate into multiple cell types of the three germ layers.

Pluripotent stem cells cultured on Matrigel and Synthemax were observed to lose their stem cell like nature; this was the case especially for the cells at the edges of the colonies, and sometimes the entire colony. Routinely, researchers avoided these differentiated cells by a process called "colony picking", in which only the undifferentiated colonies were picked up and expanded for downstream applications. When the pluripotent stem cells were cultured on NP1 and NP2, the differentiated cells would not attach to the substrates, leaving only the pluripotent colonies growing on the substrates. As result, "colony picking" was not required when NP1 and NP2 substrates were employed. This ease of culturing stem cells on the nanoparticulate surface would be a very beneficial feature in practical applications. The uniform growth of HUES-7 cells on NP1 and NP2 substrates could be clearly seen in the digital photographs (FIG. 12).

Example 3

Effect of Culture Media

The culture conditions stated above was mainly performed with mTesR1 media, which contained bovine serum albumin (BSA) as a supplement. To study if the nanoparticle coatings would be useful in translational applications whereby animal-derived components were avoided, the compatability of these synthetic substrates with xeno-free culture conditions were examined. Three xeno-free media for pluripotent stem cell culture were investigated, mTesR2 (from Stem Cell Technologies of Singapore), Nutristem (from Stemgent of Massachusetts of the United States of America) and Essential-8 (E8, from Invitrogen of California of the United States of America).

Examination of initial cell attachment within 24 hours of seeding suggested that both NP1 and NP2 substrates were able to support the xeno-free culture of pluripotent stem cells (FIG. 13). Both nanoparticle coatings performed well, but NP2 performed better in terms of cell attachment compared to NP1 in all the media tested. It was also noted that cell attachment was better with the xeno-free media. A robust attachment of cells was observed within 2 hours of seeding under the xeno-free conditions (data not shown). The pluripotency of cells cultured under xeno-free conditions for 3 passages were examined by FACS (Table 7). E8 media was noticed to support the culture with the highest number of positive cells.

TABLE 7

Expansion of HUES-7 cells was carried out for 5 passages with xeno-free media, mTesR2, Nutristem and Essential 8. At passage 5, the cells were analyzed for pluripotency using antibodies against Nanog, Oct3 and TRA 1-60 by FACS. The percentage of cells tested positive for each antibody was tabulated.

| | mTesR2 | | | Nutristem | | | Essential 8 | | |
|---|---|---|---|---|---|---|---|---|---|
| | Nanog | Oct3 | TRA 1-60 | Nanog | Oct3 | TRA 1-60 | Nanog | Oct3 | TRA 1-60 |
| NP1 | 89 | 98 | 85 | 99 | 89 | 61 | 96 | 90 | 97 |
| NP2 | 89 | 91 | 81 | 92 | 97 | 77 | 93 | 92 | 85 |

The proliferation of the pluripotent stem cells on nanoparticulate surfaces was compared with that on Matrigel and Synthemax substrates. Proliferation of pluripotent stem cells on NP1 and NP2 was observed to be slower than that on Matrigel and Synthemax in mTesR1 media (FIG. 14a). However, no significant difference in cell proliferation rate was observed on NP1, NP2, Matrigel and Synthemax in the xeno-free mTesR2 media (FIG. 14b). The doubling time for HUES-7 and DF 6-99 was calculated and tabulated in FIG. 14c. The doubling time was reduced significantly under xeno-free conditions for the NP1 and NP2 surfaces, as compared to that under mTesR1 media.

Example 4

Gene Expression Profile

In order to explore the mechanism involved in pluripotent stem cell culture on nanoparticulate substrates, the expression of the critical ECM genes and integrin subunits involved was analyzed. The expression profiles of ECM genes were similar for HUES-7 and DF 6-99 cell lines. The expression of CTGF (connective tissue growth factor) for cells cultured on NP1 and NP2 was lower compared to that on Matrigel and Synthemax (FIG. 15a and FIG. 16a). ECM proteins regulate the stem cell differentiation; the observed reduced expression of ECM genes could potentially protect the pluripotent stem cells against undergoing differentiation.

Apart from this, expressions of ECM genes were observed to be mostly higher for cells cultured on NP1 surface than that on NP2 surface (FIG. 15a). The mechanism behind these observations still needs to be explored. The ability of the nanoparticulate surfaces to support stem cell's self-renewal would also involve regulation of gene expression from "outside-to-inside" of the cell, as mediated by integrins. To identify the integrins associated with attachment to NP1 and NP2 substrates and their possible role in the gene regulation leading to pluripotency maintenance, the various integrin subunits associated with cells cultured on Matrigel, Synthemax, NP1 and NP2 were profiled. Results indicated that subunits such as ITG-α5, ITG-α6, ITG-αV, ITG-β1 and ITG-β5 were highly expressed for cells cultured all the substrates, with varying levels of expression between the substrates (FIG. 15b). A similar observation was made with DF 6-99 cell line (FIG. 16b).

CONCLUSION

The above examples demonstrated the development and application of synthetic, chemically defined nanoparticulate surfaces for the self-renewal of hESCs and hiPSCs. Cell lines of hESCs (H1 and HUES-7) and hiPSCs (hFib2-iPS4 and DF 6-99) were successfully maintained on amine and positively charged nanoparticulate surfaces for 25 serial passages in defined xeno-free medium. Pluripotent stem cells cultured on nanoparticulate surfaces retained stable doubling time, typical morphology of human pluripotent stem cells, stem cell marker expression, in vitro and in vivo pluripotency and normal karyotype.

INDUSTRIAL APPLICABILITY

The disclosed cell culture substrates can be used for the propagation of stem cells of interest. The disclosed cell culture substrates can be used for large-scale production of human embryonic stem cells and induced pluripotent stem cells for regenerative medicine.

The cell culture substrate can be used for tissue engineering, and where suitable, in drug delivery, implants, biosensors and microfluidic systems.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A cell culture substrate comprising: a substrate having a coating of a plurality of amine functionalized nanoparticles thereon, wherein said amine functionalized nanoparticle is a polymer of an acrylamide monomer, a cross-linker and an amine monomer, and
wherein said amine functionalized nanoparticles have a positive charge.

2. The cell culture substrate according to claim 1, wherein said amine functionalized nanoparticles have a particle size in the range of 50 to 200 nm.

3. The cell culture substrate according to claim 1, wherein said coating is hydrophilic.

4. The cell culture substrate according to claim 1, wherein said polymer has a molecular weight of 100 kDa to 300 kDa.

5. The cell culture substrate according to claim 1, wherein said coating has a thickness of 50 nm to 200 nm.

6. The cell culture substrate according to claim 1, wherein said amine functionalized nanoparticles have thiol terminal groups.

7. A method of making a cell culture substrate comprising a substrate having a coating of a plurality of positively charged amine functionalized nanoparticles thereon, said method comprising: an operation of spreading said plurality of positively charged amine functionalized nanoparticles onto said substrate, wherein said positively charged amine functionalized nanoparticle is a polymer of an acrylamide monomer, a cross-linker and an amine monomer.

8. The method according to claim 7, further comprising an operation of providing said plurality of positively charged amine functionalized nanoparticles in a fluid medium, thereby forming a suspension of said positively charged amine functionalized nanoparticles.

9. The method according to claim 8, wherein said suspended positively charged amine functionalized nanoparticles are present at a concentration from 2 mg/ml to 20 mg/ml.

10. The method according to claim 7, further comprising an operation of drying said positively charged amine functionalized nanoparticles after the nanoparticles are spread onto said substrate.

11. The method according to claim 7, wherein said positively charged amine functionalized nanoparticles have thiol terminal groups.

12. The method according to claim 11, further comprising an operation of functionalizing said substrate with a silane containing compound to form terminal functional groups on the surface of said substrate, wherein said terminal functional groups are capable of forming covalent linkages with said thiol-terminated positively charged nanoparticles.

13. The method according to claim 11, wherein said spreading step comprises an operation of reacting said functionalized substrate with said thiol-terminated positively charged nanoparticles.

14. The method according to claim 7, wherein said cross-linker is present at a concentration of 2.5 mol % to 15 mol %.

15. The method according to claim 7, wherein said amine monomer is present at a concentration of 2.5 mol % to 15 mol %.

16. The method according to claim 7, further comprising an operation of sterilizing said cell culture substrate.

17. The method according to claim 7, further comprising an operation of obtaining positively charged amine functionalized nanoparticles by reacting a plurality of amine functionalized nanoparticles with an acid.

18. A method of culturing stem cells, comprising:
culturing stem cells in the presence of a culture medium, the stem cells cultured on a cell culture substrate, wherein said cell culture substrate comprises a substrate having a coating of a plurality of amine functionalized nanoparticles thereon, wherein said amine functionalized nanoparticle is a polymer of an acrylamide monomer, a cross-linker and an amine monomer, and
wherein said amine functionalized nanoparticles have a positive charge.

19. The method according to claim 18, further comprising passaging said cultured stem cells.

20. The method according to claim 18, wherein said amine functionalized nanoparticles have thiol terminal groups.

* * * * *